US011661579B2

(12) United States Patent
Katayama et al.

(10) Patent No.: US 11,661,579 B2
(45) Date of Patent: May 30, 2023

(54) CELL CULTURE METHOD USING AMINO ACID-ENRICHED MEDIUM

(71) Applicant: CHUGAI SEIYAKU KABUSHIKI KAISHA, Tokyo (JP)

(72) Inventors: Satoshi Katayama, Tokyo (JP); Shouhei Kishishita, Tokyo (JP); Kunihiko Kodaira, Tokyo (JP); Makoto Sadamitsu, Utsunomiya (JP); Yoshinori Takagi, Tokyo (JP); Hiroki Matsuda, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 259 days.

(21) Appl. No.: 16/297,086

(22) Filed: Mar. 8, 2019

(65) Prior Publication Data

US 2019/0276795 A1    Sep. 12, 2019

Related U.S. Application Data

(62) Division of application No. 12/451,003, filed as application No. PCT/JP2008/058046 on Apr. 25, 2008, now abandoned.

(30) Foreign Application Priority Data

Apr. 26, 2007    (JP) .............................. JP2007-117426

(51) Int. Cl.
| C12N 5/00 | (2006.01) |
| C07K 16/28 | (2006.01) |
| C07K 16/30 | (2006.01) |
| C12P 21/02 | (2006.01) |

(52) U.S. Cl.
CPC ........ *C12N 5/0018* (2013.01); *C07K 16/2866* (2013.01); *C07K 16/303* (2013.01); *C12P 21/02* (2013.01); *C07K 2317/24* (2013.01); *C12N 2500/32* (2013.01); *C12N 2500/33* (2013.01); *C12N 2510/02* (2013.01)

(58) Field of Classification Search
None
See application file for complete search history.

(56) References Cited

U.S. PATENT DOCUMENTS

| 5,641,678 | A | 6/1997 | Ramos et al. |
| 6,048,728 | A | 4/2000 | Inlow et al. |
| 6,103,529 | A | 8/2000 | Price et al. |
| 6,900,056 | B2 | 5/2005 | Lee et al. |
| 7,709,229 | B2 | 5/2010 | Casatorres Hernandez et al. |
| 2003/0087372 | A1 | 5/2003 | Delacruz et al. |
| 2004/0229319 | A1 | 11/2004 | Egen et al. |
| 2006/0121568 | A1 | 6/2006 | Drapeau et al. |
| 2008/0108553 | A1 | 5/2008 | Luan et al. |
| 2009/0191591 | A1 | 7/2009 | Tabuchi et al. |
| 2011/0207174 | A1 | 8/2011 | Katayama et al. |
| 2012/0077213 | A1 | 3/2012 | Pla et al. |

FOREIGN PATENT DOCUMENTS

| AU | 614999 B2 | 5/1989 |
| CN | 1908162 A | 2/2007 |
| DE | 37 34 632 A1 | 4/1999 |
| EP | 0 481 791 A2 | 4/1992 |
| EP | 0 513 738 A2 | 11/1992 |
| EP | 1 132 465 A1 | 9/2001 |
| EP | 1 229 125 A1 | 8/2002 |
| EP | 2 351 833 A1 | 8/2011 |
| GB | 2 251 249 A | 7/1992 |
| IE | 921020 A1 | 11/1992 |
| JP | 01-231887 A | 9/1989 |
| JP | 04-501660 A | 3/1992 |
| JP | 05-252942 A | 10/1993 |
| JP | 2006-296282 A | 11/2006 |
| WO | WO 90/03430 A1 | 4/1990 |
| WO | WO 91/12316 A1 | 8/1991 |
| WO | WO-98/45411 A1 | 10/1998 |
| WO | WO 02/33109 A2 | 4/2002 |
| WO | WO-02/101019 A2 | 12/2002 |
| WO | WO 2004/099396 A1 | 11/2004 |
| WO | WO 2006/026408 A2 | 3/2006 |
| WO | WO-2006/026445 A1 | 3/2006 |
| WO | WO-2006/026447 A2 | 3/2006 |
| WO | WO 2006/050050 A2 | 5/2006 |
| WO | WO2007119774 | * 3/2007 |
| WO | WO-2008/063892 A2 | 5/2008 |

OTHER PUBLICATIONS

International Search Report dated Aug. 5, 2008, in PCT/JP2008/058046, 1 page.
Kuwae et al., "Development of a Fed-Batch Culture Process for Enhanced Production of Recombinant Human Antithrombin by Chinese Hamster Ovary Cells," Journal of Bioscience and Bioengineering, 2005, 100(5):502-510.
Written Opinion of the Hungarian Patent Office dated Jan. 5, 2011, in corresponding Singapore patent application No. 200907038-4, 17 pages.
Supplementary European Search Report dated Jul. 12, 2011, in corresponding EP 08752120.9, 11 pages.
Franek et al., "Unbalanced media for hybridoma cell culture—an alternative reality," Animal Cell Technology, Jan. 1, 1997, 675-680.
Baker et al., Animal Cell Technology, 1999, pp. 263-265.

(Continued)

*Primary Examiner* — Michail A Belyavskyi
(74) *Attorney, Agent, or Firm* — Foley & Lardner LLP

(57) ABSTRACT

Methods of culturing cells capable of producing desired proteins to obtain the proteins by use of a medium from which biological components are excluded as much as possible are provided. Specifically, a culture method characterized by culturing while maintaining a specific amino acid in a culture solution at a high concentration, and a cell culture fed-batch medium for use in the method are provided.

6 Claims, 7 Drawing Sheets

Specification includes a Sequence Listing.

(56) References Cited

OTHER PUBLICATIONS

Englesberg et al., "Inhibition of the Growth of Mammalian Cells in Culture by Amino Acids and the Isolation and Characterization of L-Phenylalanine-Resistant Mutants Modifying L-Phenylalanine Transport," Somatic Cell Genetics, 1976, 2(5):411-428.

Feng et al., "Application of oxygen uptake rate-amino acids' associated mode in controlled-fed perfusion culture," Journal of Biotechnology, 2006, 122:422-430.

Jayapal et al., "Recombinant Protein Therapeutics from CHO Cells - 20 Years and Counting," Chemical Engineering and Materials Science, CHO Consortium SBE Special Section, Oct. 2007, 40-47.

Kim et al., "Development of a serum-free medium for the production of humanized antibody from Chinese hamster ovary cells using a statistical design," In Vitro Cell. Dev. Biol. - Animal, November-Dec. 1998, 34:757-761.

Kim et al., "Effects of supplementation of various medium components on Chinese hamster ovary cell cultures producing recombinant antibody," Cytotechnology, 2005, 47:37-49.

Lopes et al., "Influence of amino-acid concentration in the culture medium on the rate of amino-acid incorporation into protein and amino-acid oxidation of cultured chicken hepatocytes," Reprod. Nutr. Dev., 1994,34:157-164.

Lubiniecki et al., "Historical reflections on cell culture engineering," Cytotechnology, 1998, 28:139-145.

Molowa et al., "The state of biopharmaceutical manufacturing," Biotechnology Annual Review, 2003, 9:285-302.

Nishiuch et al., "Cytotoxicity of cysteine in culture media," In Vitro, 1976, 12(9):635-638.

Printout of the homepage of Uppsala University, Apr. 26, 2019, 5 pages.

Pybus et al., "Predicting the Expression of Recombinant Monoclonal Antibodies in Chinese Hamster Ovary Cells Based on Sequence Features of the CDR3 Domain," Biotechnol. Prog., 2014, 30:188-197.

Salazar et al., "Amino acids in the cultivation of mammalian cells," Amino Acids, 2016, 48:1161-1171.

Svensson, Erik, "Improvement of a CHO cell process by feeding peptones," Master's degree project, Aug. 2006, 57 pages.

Whitford, William G., "Fed-Batch Mammalian Cell Culture in Bioproduction," BioProcess International, Apr. 2006, 30-40.

Wlaschin et al., "Fedbatch Culture and Dynamic Nutrient Feeding," Adv. Biochem. Engin./Biotechnol., 2006, 101:43-74.

\* cited by examiner

Figure 9

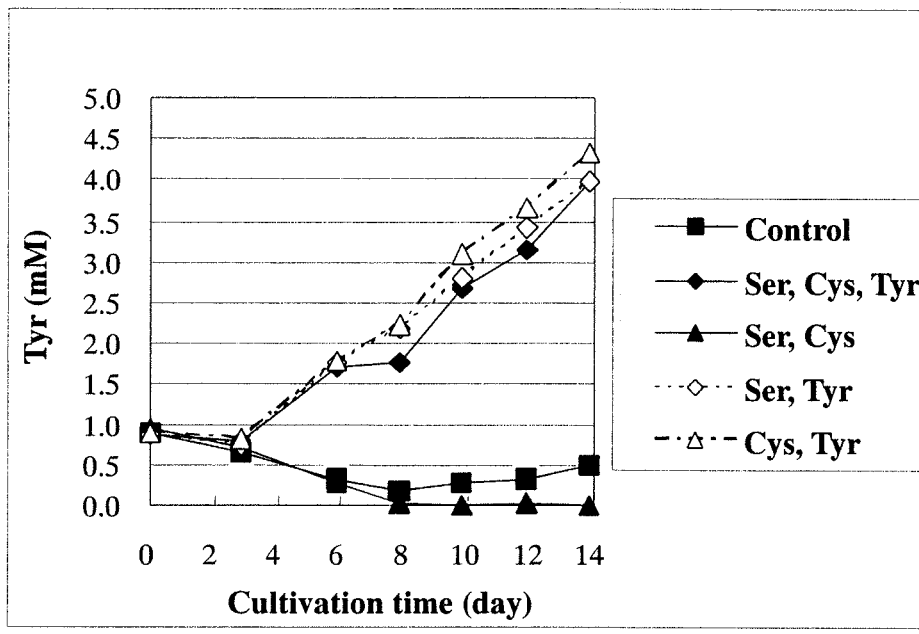

Figure 10

```
          10         20         30         40         50         60         70         80         90        100        110        120        130        140        150
atggccaccaaggagaagctgcagtgtctgaaagacttccacaaagacatcctgaagccttctccagggaagagccaggcacacggcctgaggatgaggctgagggagaaagccccctcagagggagaagtggtccagcaagattgacttt
M  A  T  K  E  K  L  Q  C  L  K  D  F  H  K  D  I  L  K  P  S  P  G  K  S  P  G  T  R  P  E  D  E  A  E  G  K  P  P  Q  R  E  K  W  S  S  K  I  D  F
         160        170        180        190        200        210        220        230        240        250        260        270        280        290        300
gtgctgtctgtggccggaggcttcgtggggtttgggcaacgtttggcgtttcccgtacctctgctacaaaatggtggaggtgctttccctcataccgtattttattttcctgtttggagtggcctgcctgtgtttttcctggaggtcata
V  L  S  V  A  G  G  F  V  G  L  G  N  V  W  R  F  P  Y  L  C  Y  K  N  G  G  A  F  L  I  P  Y  F  I  F  L  F  G  S  L  P  V  F  F  L  E  V  I
         310        320        330        340        350        360        370        380        390        400        410        420        430        440        450
ataggccagtacacctcagaagggggaatcacctgctgggagaagatctgccccttgttctctggcattggctacgcatccatcgtcatcgtgtccctcctgaatgtgtactacattgtcatcctggcctggccacatactacctattt
I  G  Q  Y  T  S  E  G  G  I  T  C  W  E  K  I  C  P  L  F  S  G  I  G  Y  A  S  I  V  I  V  S  L  L  N  V  Y  Y  I  V  I  L  A  W  A  T  Y  Y  L  F
         460        470        480        490        500        510        520        530        540        550        560        570        580        590        600
cactcctttccagacagagcttccctgggccactgcaaccacagctggaacacaccacattgcatggaggacacctgctgaggaatgagagtctctgggtctccttagcgcctccaacttcacctcgcctgtcatcgagttctgggag
H  S  F  Q  T  E  L  P  W  A  H  C  N  H  S  W  N  T  P  H  C  M  E  D  T  L  R  R  N  E  S  L  W  V  S  L  S  A  S  N  F  T  S  P  V  I  E  F  W  E
         610        620        630        640        650        660        670        680        690        700        710        720        730        740        750
cgcaatgtactcagcctgtcttccggaatcgacgaaccaggcgctctgaaatgggaccttgcgctctgcctcctcttagtctggcttgtctgttttttctgcatatgaaggtgttcgatccacaggcaaggttgtctacttcaccgcc
R  N  V  L  S  L  S  S  G  I  D  E  P  G  A  L  K  W  D  L  A  L  C  L  L  L  V  W  L  V  C  F  F  C  I  W  K  G  V  R  S  T  G  K  V  V  Y  F  T  A
         760        770        780        790        800        810        820        830        840        850        860        870        880        890        900
actttcccgtttgccatgctctctggtgctgctggtccgtggactgaccctgccgggtgctggcgaaggcatcaaattctaccgtgaccctgacatcagccgccttgaggaccacaggtgtggatcgacgccggaacccagatattcttt
T  F  P  F  A  M  L  L  V  L  L  V  R  G  L  T  L  P  G  A  E  G  I  K  F  Y  L  Y  P  D  I  S  R  L  E  D  P  Q  V  W  I  D  A  G  T  Q  I  F  F
         910        920        930        940        950        960        970        980        990       1000       1010       1020       1030       1040       1050
tcctatgccatctgcctggggcccatgacctcactgggaagctacaacaagtacaagtataactcgtacagggactgtatgctgctgggatgccgaacagtggtaccagttttgtgtctggccttcgcagtttttccatcctgggcttc
S  Y  A  I  C  L  G  A  M  T  S  L  G  S  Y  N  K  Y  K  Y  N  S  Y  R  D  C  M  L  L  G  C  L  N  S  G  T  S  F  V  S  G  F  A  V  F  S  I  L  G  F
        1060       1070       1080       1090       1100       1110       1120       1130       1140       1150       1160       1170       1180       1190       1200
atggcacaagagcaaggggtggacattgctgatggctgagtcaggtcctggcttggccttcattgcctatccaaaagctgtgactatgatgccgctgccaccttttggtccattctgttttttattatgctcctcttgcttggactg
M  A  Q  E  Q  G  V  D  I  A  D  V  A  E  S  G  P  G  L  A  F  I  A  Y  P  K  A  V  T  M  M  P  L  P  T  F  W  S  I  L  F  F  I  M  L  L  L  L  G  L
        1210       1220       1230       1240       1250       1260       1270       1280       1290       1300       1310       1320       1330       1340       1350
gacagccagtttgttgaagtcgaaggacagatcacatccttggttgatctttacccgtccttcttaaggaagggttatcgtcgggaagtcttcatcgccatcctgtgtagcatcagctacctgctggggctgtcgatggtgacggaggt
D  S  Q  F  V  E  V  E  G  Q  I  T  S  L  V  D  L  Y  P  S  F  L  R  K  G  Y  R  R  E  V  F  I  A  I  L  C  S  I  S  Y  L  L  G  L  S  M  V  T  E  G
        1360       1370       1380       1390       1400       1410       1420       1430       1440       1450       1460       1470       1480       1490       1500
ggcatgtatgtgtttcaactctttgactactatgcagctagtggtgtatgcctttttgtggtgttgcattcttgaatgtttttgttattgcctggatatatgtggtgataactttatatgacggtattgaggacatgattggctatcggcct
G  M  Y  V  F  Q  L  F  D  Y  Y  A  A  S  G  V  C  L  L  W  V  A  F  F  E  C  F  V  I  A  W  I  Y  G  G  D  N  L  Y  D  G  I  E  D  M  I  G  Y  R  P
        1510       1520       1530       1540       1550       1560       1570       1580       1590       1600       1610       1620       1630       1640       1650
gggccctggatgaagtacagctgggctgtcatcactccagttctctgtgctggatgttttcatcttctcctcttgtcaagtatgtaccccctacaacaaagtctacgtgtatcctgattgggcaattgggctgggctgggcctgccc
G  P  W  M  K  Y  S  W  A  V  I  T  P  V  L  C  A  G  C  F  I  F  S  L  V  K  Y  V  P  L  T  Y  N  K  V  Y  V  Y  P  D  W  A  I  G  L  G  W  G  L  A
        1660       1670       1680       1690       1700       1710       1720       1730       1740       1750       1760       1770       1780       1790       1800
ctatcctccatggtgtgtatccccttggtcattgccatcctcctctgccgacggagggaccgttccgcgtgagaatccaataccgataaccccaggagccaaccgctgggctgtggagcgtgaggggcacaccctccactcc
L  S  S  M  V  C  I  P  L  V  I  A  I  L  L  C  R  T  E  G  P  F  R  V  R  I  Q  Y  L  I  T  P  R  E  P  N  R  W  A  V  E  R  E  G  A  T  P  F  H  S
        1810       1820       1830       1840       1850       1860       1870
cgcacaagcctcgtcatgaacggcgcactcatgaaacccagtcacgtcattgtggagaccatgatgtga
R  T  S  L  V  M  N  G  A  L  M  K  P  S  H  V  I  V  E  T  M  M  *
```

CELL CULTURE METHOD USING AMINO ACID-ENRICHED MEDIUM

CROSS REFERENCE TO RELATED APPLICATIONS

This application is a Divisional Application of U.S. application Ser. No. 12/451,003 filed Oct. 22, 2009 which is a U.S. National Stage application of PCT/JP2008/058046, filed on Apr. 25, 2008, which claims priority from Japanese Patent application No. 2007-117426, filed on Apr. 26, 2007, the entire disclosures of all of which are incorporated herein by reference.

The instant application contains a Sequence Listing which has been submitted in ASCII format via EFS-WEB and is hereby incorporated by reference in its entirety. Said ASCII copy, created on May 17, 2019, is named sequence.txt and is 14,726 bytes.

TECHNICAL FIELD

The present invention relates to methods of culturing cells capable of producing desired proteins to obtain the proteins, and media for use in the methods. In particular, the present invention relates to methods of culturing cells capable of producing desired proteins to obtain the desired proteins and to methods of producing proteins by a serum-free culture method, characterized in that serine in a liquid culture is maintained at a high concentration. The present invention further relates to cell culture fed-batch media for use in the methods.

BACKGROUND ART

When a natural protein produced by an animal cell was to be obtained by culturing the animal cell, or when a desired protein or the like was to be prepared by culturing an animal cell transformed with a gene encoding the desired protein, the culture medium had to be supplemented in the range of 5-20% with an extract derived from a mammal, specifically a serum such as fetal calf serum, for the growth of the animal cell, in addition to basic nutrients such as salts, sugars, amino acids, and vitamins. The sera derived from mammals, however, entailed disadvantages that such mammal-derived sera account for 75-95% of the cost of media, and that stable growth cannot be achieved due to variation in quality among lots. Furthermore, since sera derived from mammals cannot be sterilized by an autoclave or the like, there is a possibility of contamination with viruses or mycoplasmas; although many of them are harmless, they may become additional unknown factors from the viewpoint of stable production.

In recent years, there has been great concern that components derived from mammals may be associated with mad cow disease, or Bovine Spongiform Encephalopathy (BSE), Transmissible Spongiform Encephalopathy (TSE), and, furthermore, Creutzfeld-Jakob Disease (CJD), and in view of safety, an animal cell culture medium free from mammalian components has been sought. Further, a serum contains at least 500 types of proteins, and this complicates isolation/purification of a desired protein as a bio-product from a cell culture medium.

To solve the above problems, serum-free culture methods suitable for culturing animal cells in the absence of a serum have been developed. In the development of serum-free culture methods, serum-free liquid media containing, as substitutes for the effect of sera, plasma proteins such as fetuin, transferrin, and albumin, hormones such as steroid hormone and insulin, growth factors, and nutrient factors such as amino acids and vitamins have been provided.

Fetuin, insulin, transferrin, and growth factors for use in serum-free culture methods are purified proteins derived from sera or recombinant proteins derived from recombinant organisms. Use thereof has the following disadvantages: though small in amount, biological components are contained; use of an expensive product is required; culture varies among lots; and the like.

In recent years, serum-free culture methods using protein hydrolysates have been developed. Such culture methods have similar disadvantages as stated above: a component derived from an organism is contained; costs are high; production varies among different lots; and the like. Thus it is difficult to say that such serum-free culture methods are most adequate for the production of useful proteins.

In view of the foregoing, there have been demands for a culture method using a chemically defined medium that contains as few biological components as possible, is inexpensive, causes small variation among lots, and can result in a boost in protein production. Recently, behavior of glucose and amino acids in a culture solution in fed-batch culture was analyzed, and this analysis revealed that use of an increased amount of glutamate in fed-batch culture contributed to increase in an amount of antithrombin that was produced (Non-patent Document 1). However, this finding is only based on specific CHO cells expressing glutamine synthetase, and no demonstration using general CHO cells has been performed. Furthermore, individual effects of other amino acids have not been investigated. Further, amounts of proteins that are produced are still not sufficient. Thus there have been strong demands for a development of a culture process using a chemically defined medium that is capable of offering more enhanced protein production.

Non-patent Document 1: Journal of Bioscience and Bioengineering (2005), 100(5), 502-510

DISCLOSURE OF THE INVENTION

Problems to be Solved by the Invention

The present invention is applicable to a fed-batch culture method using a medium in which biological medium components are reduced to a minimum, and aims to provide an improved medium so that when cells are cultivated by fed-batch culture using the medium, the cells produce proteins at a high yield.

Means for Solving the Problems

The present inventors extensively and intensively studied to solve the above problems. Consequently, they found that specific amino acids were frequently depleted and that maintaining such amino acids at high concentrations in a serum-free liquid culture enabled cells to produce proteins at a high yield. By this finding, the present invention was completed.

Specifically, the present invention provides:

(1) a method of culturing a cell characterized in that a concentration of serine in a culture solution is maintained at 1 mM or higher at least during a certain period after the onset of a cell growth phase, the method used in a process comprising culturing a cell that is capable of producing a desired protein to obtain the desired protein;

(2) the method (1) further characterized in that a concentration of tyrosine in the culture solution is maintained at 1 mM or higher, and/or a concentration of cysteine in the culture solution is maintained at a concentration of the cysteine in an initial medium or at 0.4 mM or higher at least during the certain period after the onset of the cell growth phase;

(3) a medium for animal cell culture, comprising at least 1 mM of serine or a salt thereof;

(4) a medium for animal cell culture, comprising at least 1 mM of serine or a salt thereof, and further comprising at least 1 mM of tyrosine and/or at least 0.4 mM of cysteine;

(5) a process of producing a desired protein, comprising culturing a cell capable of producing the desired protein, by use of the medium (3) or (4) to obtain the desired protein;

(6) a method of culturing a cell, the method used in a process comprising culturing a cell that is capable of producing a desired protein to obtain the desired protein, the method characterized in that a concentration of serine in a culture solution is maintained at 1 mM or higher at least during a part of or an entire period sufficient to enable the cell that is to be cultured to grow sufficiently, or during a part of or an entire period sufficient to enable adequate production of the desired protein that is to be produced;

(7) the method (6) further characterized in that a concentration of tyrosine in the culture solution is maintained at 1 mM or higher, and/or a concentration of cysteine in the culture solution is maintained at a concentration of the cysteine in an initial medium or at 0.4 mM or higher at least during a part of or the entire period sufficient to enable the cell that is to be cultured to grow sufficiently, or during a part of or the entire period sufficient to enable adequate production of the desired protein that is to be produced;

(8) a method of culturing a cell characterized in that a concentration of serine in a culture solution is maintained at 1 mM or higher at least during a part of or an entire period of an exponential cell growth phase, the method used in a process comprising culturing a cell that is capable of producing a desired protein to obtain the desired protein;

(9) the method (8) further characterized in that a concentration of tyrosine in the culture solution is maintained at 1 mM or higher, and/or a concentration of cysteine in the culture solution is maintained at a concentration of the cysteine in an initial medium or higher or at 0.4 mM or higher at least during a part of or an entire period of the exponential cell growth phase;

(10) the method (8) or (9), wherein the concentration of serine in the culture solution is maintained at 2 mM or higher at least during a part of or an entire period of the exponential cell growth phase;

(11) a method of culturing a cell characterized in that a concentration of serine in a culture solution is maintained at 1 mM or higher at least during a part of or an entire period from a third day to a tenth day of the culture, the method used in a process comprising culturing a cell that is capable of producing a desired protein to obtain the desired protein;

(12) the method (11) further characterized in that a concentration of tyrosine in the culture solution is maintained at 1 mM or higher, and/or a concentration of cysteine in the culture solution is maintained at a concentration of the cysteine in an initial medium or higher or at 0.4 mM or higher at least during a part of or an entire period from the third day to the tenth day of the culture;

(13) the method (11) or (12), wherein the concentration of serine in the culture solution is maintained at 2 mM or higher at least during a part of or an entire period from the third day to the tenth day of the culture;

(14) any one of the methods or processes (1), (2), and (5)-(13), wherein the cell is cultured by batch culture, repeated batch culture, fed-batch culture, repeated fed-batch culture, continuous culture, or perfusion culture;

(15) any one of the methods or processes (1), (2), and (5)-(13), wherein the cell is cultured by fed-batch culture;

(16) the method or process (15), wherein the serine and tyrosine and/or cysteine are fed into the culture solution in multiple batches sequentially or continuously;

(17) any one of the methods or processes (1), (2), and (5)-(16), wherein the cell is transformed with a gene encoding the desired protein;

(18) the method or process (17), wherein the desired protein is an antibody;

(19) any one of the methods or processes (1), (2), and (5)-(18), wherein the cell is a mammal cell;

(20) the method (19), wherein the mammal cell is CHO cell;

(21) a fed-batch medium for culturing a cell, comprising serine at a concentration of 10 mM to 1000 mM;

(22) a fed-batch medium for culturing a cell, comprising serine at a concentration of 20 mM to 500 mM;

(23) the fed-batch medium (21) or (22), further comprising cysteine and/or tyrosine;

(24) the fed-batch medium (21) or (22), further comprising cysteine and tyrosine;

(25) a method of culturing a cell by fed-batch culture, comprising adding any one of the fed-batch media (21)-(24);

(26) a process of producing a desired protein by culturing a cell, comprising culturing a cell using any one of the methods (1), (2), and (6)-(20); and

(27) a preparation process of a medicament comprising as an active ingredient a protein produced by the process (5) or (26).

Advantages of the Invention

The present invention can be conveniently used in the production of physiologically active peptides or proteins. A feature of the present invention is that cultivation using a chemically defined medium free from biological components is made more productive of proteins. Furthermore, because the fed-batch medium for use in the present invention contains significantly pure amino acids, the medium composition is clearly defined, and the medium is of uniform properties with less variations among lots. Use of the medium ensures that a protein of uniform properties would be obtained as well, thus the medium is suitable for industrial manufacture. Specifically, the medium greatly contributes to, for example, mass supply of antibodies for a pharmaceutical use.

BRIEF DESCRIPTION OF THE DRAWINGS

FIG. 9 shows the transition of concentrations of tyrosine during the culture period. (Example 3)

FIG. 10 shows the amino acid sequence (SEQ ID NO: 2) of a hamster taurine transporter and the nucleotide sequence (SEQ ID NO: 1) of a gene encoding the same. (Reference Example 1)

EMBODIMENT OF THE INVENTION

Figure 1:
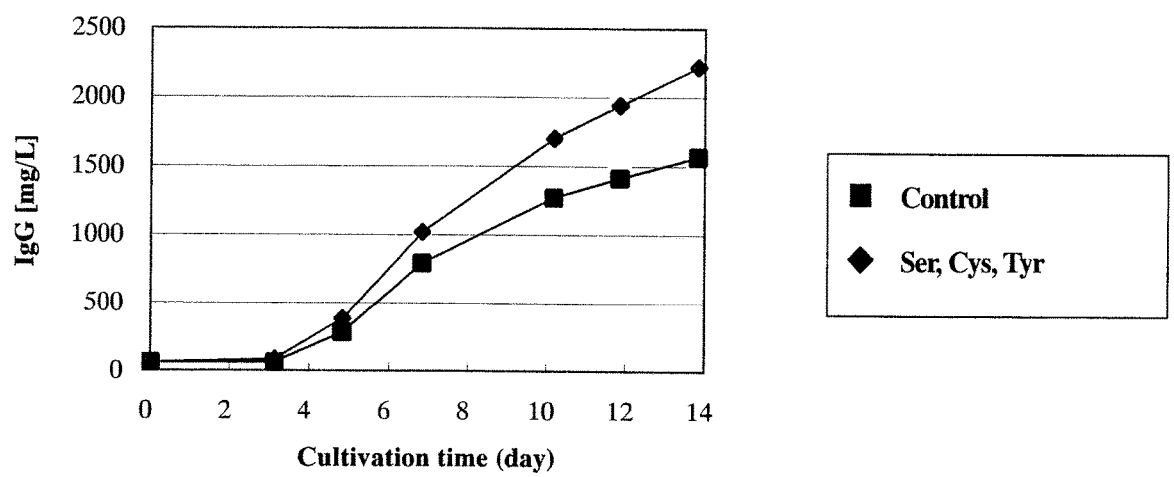
FIG. 1 shows the transition of concentrations of antibodies during the culture period. (Example 1)

The following specifically describes embodiments of the present invention.

A method of the present invention is characterized by comprising maintaining, when cells capable of producing desired proteins are cultured to obtain the proteins, serine in a culture solution at a high concentration. Specifically, the method is characterized by maintaining the concentration of serine in the culture solution at 1 mM or higher, preferably 2 mM or higher, at least during a certain period of time after a cell growth phase has started.

Accordingly, one aspect of the present invention is an animal cell culture medium comprising at least 1 mM of serine or a salt thereof. In the present invention, the expression "animal cell culture medium comprising at least 1 mM of serine (or a salt thereof)" refers to not only a medium comprising serine at a concentration of 1 mM or higher in an initial medium but also a medium adjusted such that a concentration of serine in the culture solution is maintained at 1 mM or higher, preferably 2 mM or higher, by addition of a fed-batch medium or the like at least during a certain period from or after the onset of the cell growth phase.

The method of the present invention is characterized by further comprising supplementing the culture solution with tyrosine and/or cysteine, in addition to serine contained at a high concentration. Specifically, the concentration of tyrosine in the culture solution is maintained at 1 mM or higher and/or the concentration of cysteine is maintained at a concentration of the cysteine in the initial medium or higher at least during a certain period from or after the onset of a cell growth phase. Since the concentration of cysteine in the initial medium is normally about 0.4 mM, the concentration of cysteine in the culture solution may be 0.4 mM or higher, preferably 1 mM or higher, at least during a certain period from or after the start point of the cell growth phase, regardless of the concentration of cysteine in the initial medium.

Accordingly, another aspect of the present invention is an animal cell culture medium comprising 1 mM or higher of serine or a salt thereof, and at least 1 mM or higher of tyrosine and/or 0.4 mM or higher of cysteine. In the present invention, the expression "animal cell culture medium comprising at least 1 mM of tyrosine" refers to not only a medium comprising tyrosine at a concentration of 1 mM or higher in an initial medium but also a medium adjusted such that a concentration of tyrosine in the culture solution is maintained at 1 mM or higher by addition of a fed-batch medium or the like at least during a certain period from or after the onset of the cell growth phase. Similarly, the expression "animal cell culture medium comprising at least 0.4 mM of cysteine" refers to not only a medium comprising cysteine at a concentration of 0.4 mM or higher in an initial medium but also a medium adjusted such that a concentration of cysteine in the culture solution is maintained at 0.4 mM or higher by addition of a fed-batch medium or the like at least during a certain period from or after the onset of the cell growth phase.

If the concentration of serine (and tyrosine and/or cysteine) in the culture solution is maintained as described above while cells are cultured, the concentration of serine (and tyrosine and/or cysteine) in the culture solution is maintained at a predetermined concentration or higher at least during a part of a period sufficient to enable cells that are to be cultured to grow sufficiently, or during a part of a period sufficient to enable adequate production of desired proteins that are to be produced, enabling the cells to produce the proteins at high yields.

Accordingly, another aspect of the present invention is a method of culturing cells capable of producing desired proteins to obtain the proteins by use of a medium adjusted such that a concentration of serine (and tyrosine and/or cysteine) is maintained at a predetermined concentration or higher. Accordingly, another aspect of the present invention is a process of producing desired proteins, which process is characterized by comprising culturing cells capable of producing the desired proteins by use of an animal cell culture medium comprising at least 1 mM of serine or a salt thereof. Another aspect of the present invention is a method of producing desired proteins, which method is characterized by comprising culturing cells capable of producing the desired proteins by use of an animal cell culture medium comprising at least 1 mM of serine or a salt thereof, at least 1 mM of tyrosine, and/or at least 0.4 mM of cysteine.

In the present invention, the period during which the concentration of serine (and tyrosine and/or cysteine) in the culture solution is maintained at a predetermined concentration or higher as described above may be a part of a period from the start point to the end point of the growth phase, or an entire period from the start point to the end point of the growth phase, or an entire culture period.

The expression "onset (or start point) of a growth phase" as used herein refers to a transition period from a lag phase to an accelerated phase of growth of cultured cells. Thereafter, the phase moves from the accelerated phase to an exponential growth phase, a decline phase, a stationary phase, and then a death phase. (Takeshi Kobayashi and Hiroyuki Honda, "*Seibutsukagakukogaku*" (Biochemical Engineering), Tokyo Kagaku Dojin, Applied Life Science Series 8, 2002.)

In another aspect of the present invention, the period during which the concentration of serine (and tyrosine and/or cysteine) in the culture solution is maintained at a predetermined concentration or higher in the culture method of the present invention may be a part of or an entire period sufficient to enable cells that are to be cultured to grow sufficiently, or a part of or an entire period sufficient to enable adequate production of desired proteins; specifically, the concentration may be maintained at a predetermined concentration or higher during a part of an entire period from the start point to the end point of the growth phase of the cells that are cultured. It is especially important to maintain the concentration of serine (and tyrosine and/or cysteine) in the culture solution at a predetermined concentration or higher during a certain period from or after the third day of the culture, because an amino acid content of the initial medium is depleted on and after the third day of the culture. Accordingly, in this aspect of the present invention, more specifically, a period in which it is required to maintain the concentration of serine (and tyrosine and/or cysteine) in the culture solution at a predetermined concentration or higher may be at least a part of or an entire period from the third day of the culture to a phase from the decline phase to the stationary phase of the cultured cells, preferably a part of or an entire period from the third day of the culture to a phase from the exponential cell growth phase to the decline phase.

In a further specific aspect, it is preferable to maintain the concentration of serine (and tyrosine and/or cysteine) in the culture solution at a predetermined concentration or higher during a period from at least 4 days after (normally on day 5 of culture) the start point of the cell growth phase (normally around day 1 of culture), preferably a period from at least 3 days after (normally on day 4 of culture) the start point of the growth phase, more preferably a period from at least 2 days after (normally on day 3 of culture) the start point of the growth phase, even more preferably a period from or after the start point of the growth phase. Further, it is required to maintain the concentration of serine (and tyrosine and/or cysteine) in the culture solution at a predetermined concentration or higher at least until 5 days before the end of the culture, preferably until 4 days before the end of the culture, more preferably until 3 days before the end of the culture, in cases in which the culture period is not longer than two weeks; in cases in which the culture period is longer than two weeks, it is required to maintain the concentration of serine (and tyrosine and/or cysteine) in the culture solution at a predetermined concentration or higher until the tenth day of the culture, preferably until 5 days before the end of the culture, more preferably until 4 days before the end of the culture, even more preferably until 3 days before the end of the culture.

In another aspect of the present invention, it is preferable to continuously maintain the concentration of serine (and tyrosine and/or cysteine) in the culture solution at a predetermined concentration or higher at least during a part of the exponential cell growth phase. A specific period is a period from 4 days after the start point of the exponential growth phase, preferably a period from 3 days after the start point of the exponential growth phase, more preferably a period from the start point of the exponential growth phase. As used herein, the expression "a part of an exponential cell growth phase" refers to a part of the exponential growth phase, an entire period from the start point to the end point of the exponential growth phase, or an entire culture period, during which the concentration may be maintained.

In typical cell culture, the start point of the exponential growth phase is normally around day 3 of culture. Accordingly, in another specific aspect of the present invention, the concentration of serine in the culture solution is maintained at 1 mM or higher, preferably 2 mM or higher, at least during a part of or an entire culture period from the third day of the culture. In cases in which the concentrations of tyrosine and/or cysteine are also maintained at predetermined concentrations or higher, the concentration of tyrosine in the culture solution is maintained at 1 mM or higher and/or the concentration of cysteine is maintained at a concentration of the cysteine in an initial medium or higher at least during a part of or an entire culture period from the third day of the culture. Since a typical concentration of cysteine in the initial medium is about 0.4 mM, the said concentration of cysteine in the culture solution may be 0.4 mM or higher, preferably 1 mM or higher, during a part of or an entire culture period from the third day of the culture, regardless of the concentration of the cysteine in the initial medium.

As used herein, the expression "at least a part of or an entire culture period from the third day of the culture" refers to a culture period from the fourth, fifth, sixth, or seventh day of the culture, or a culture period from the start point of the culture or from the first or second day of the culture including a part of or an entire culture period from the third day of the culture.

In the cases in which the culture period is not longer than two weeks, it is preferable to continuously maintain the concentration of serine (and tyrosine and/or cysteine) in the culture solution at a predetermined concentration or higher at least until 5 days before the end of the culture, preferably until 4 days before the end of the culture, more preferably until 3 days before the end of the culture. In the cases in which the culture period is longer than two weeks, it is preferable to continuously maintain the concentration of serine (and tyrosine and/or cysteine) in the culture solution at a predetermined concentration or higher at least until the tenth day of the culture, preferably until 5 days before the end of the culture, more preferably until 4 days before the end of the culture, even more preferably until 3 days before the end of the culture.

Accordingly, in another aspect of the present invention, the concentration of serine in the culture solution is maintained at 1 mM or higher, preferably 2 mM or higher, at least during a part of or an entire period from the third day to the tenth day of the culture. In the cases in which the concentrations of tyrosine and/or cysteine are also maintained at predetermined concentrations or higher, the concentration of tyrosine in the culture solution is maintained at 1 mM or higher and/or the concentration of cysteine is maintained at a concentration of the cysteine in an initial medium or higher at least during a part of or an entire period from the third day to the tenth day of the culture. Since the concentration of cysteine in the initial medium is normally about 0.4 mM, the concentration of cysteine in the culture solution may be maintained at 0.4 mM or higher, preferably 1 mM or higher, during a part of or an entire period from the third day to the tenth day of the culture, regardless of the concentration of the cysteine in the initial medium.

As used herein, the expression "at least a part of or an entire culture period from the third day to the tenth day of the culture" refers to a culture period from the fourth, fifth, sixth, or seventh day of the culture, or a culture period from the start point of the culture or from the first or second day of the culture including a part of or an entire culture period from the third day to the tenth day of the culture.

In the above aspect, it is sufficient to maintain the concentration of serine (and tyrosine and/or cysteine) in the culture solution at a predetermined concentration or higher at least during a part of or an entire period from the third day of the culture. Even when the culture period is shorter than 10 days, if the concentration of serine (and tyrosine and/or cysteine) in the culture solution is maintained at a predetermined concentration or higher during a part of or an entire period from the third day of the culture, this is encompassed within the scope of the present invention.

Culturing cells by the method of the present invention enables high-yield production of proteins that are bio-product from the cells, and the proteins are isolated from the culture medium and purified to obtain desired proteins.

Culturing cells while maintaining the concentration of serine (and tyrosine and/or cysteine) in the culture solution at a predetermined concentration can be achieved either by addition of a high concentration of serine (and tyrosine and/or cysteine) to the medium at an early stage of the cell culture, or by addition of a medium comprising a high concentration of serine (and tyrosine and/or cysteine) during the culture to supplement the medium with amino acids.

A preferred timing of commencing supplementing the culture solution with amino acids to maintain the concentration of serine (and tyrosine and/or cysteine) in the culture solution is at least within 3 days from a time when the amino acids in the culture solution reach a predetermined concentration or lower, preferably within 1 day, most preferably before the amino acids reach a predetermined concentration or lower. Supplementation of amino acids may be carried out once only, in butches sequentially, or continuously. Alternatively, the initial medium may contain a total amount of amino acids required for maintaining the amino acids at predetermined concentrations.

In general, cell culture methods are classified into batch culture, continuous culture, and fed-batch culture. In the method of the present invention, any of these culture methods can be used, but fed-batch culture or continuous culture is preferably used; use of fed-batch culture is especially preferred.

Batch culture is a culture method in which a small amount of seed culture solution is added to a medium and cells are grown without any addition of a new medium or discharge of the culture solution during the culture. In the case of using the batch culture in the present invention, the medium comprises a high concentration of serine (and tyrosine and/or cysteine) from an initial stage of the cell culture.

Continuous culture is a culture method in which a medium is added and discharged continuously during the culture. This continuous method includes perfusion culture.

Fed-batch culture is also called semi-batch culture because it is between batch culture and continuous culture. In the fed-batch culture, a medium is fed continuously or sequentially during cultivation, but unlike the continuous culture, discharge of the culture solution is not carried out in the culture. The medium to be added in the fed-batch culture (hereinafter "fed-batch medium") does not necessarily have to be the same medium as that already used in the culture (hereinafter "initial medium"); namely, a different medium may be added, or only specific components may be added.

As used herein, the term "initial medium" generally refers to a medium used in an early stage of cell culture. Note that in the case in which the fed-batch medium is added in multiple batches, each medium before the addition of the fed-batch medium may be referred to as an initial medium.

In the case of employing the fed-batch culture or continuous culture in the present invention, the medium that is to be added during the culture may contain a high concentration of serine (and tyrosine and/or cysteine), or a high concentration of serine (and tyrosine and/or cysteine) may be contained in the culture medium from an initial stage of the cell culture. What is important is to maintain the concentration of serine, or respective concentrations of serine and tyrosine, or respective concentrations of serine and cysteine, or respective concentrations of serine, tyrosine, and cysteine, at a predetermined concentration or higher at least during a predetermined stage of the culture, as described above. To realize the foregoing, for instance the concentration of serine (and tyrosine and/or cysteine) in the culture solution may be monitored to adjust the concentrations of these amino acids in the medium to be added so that the concentrations of these amino acids in the culture solution can be controlled. Alternatively, a method in which, for instance, a stage of a cell growth curve is determined on the basis of the number of cells in the culture to control the supplementation of the amino acids can be employed.

The following describes in detail serine, tyrosine, and cysteine in the culture solution, by which the present invention is characterized.

Any of serine alone, derivatives thereof, and salts thereof can be used. Natural serine, synthetic serine, or serine produced by gene recombination can be used. The concentration of serine in the culture solution is, for example, 1 mM or higher, preferably 2 mM or higher at least during a predetermined period in the culture. A conventionally used medium comprising serine typically comprises about 0.5 mM of serine; thus it is recognized that the concentration of serine in the present invention is significantly high (Dulbecco, R., Freeman, G. Virology 8, p 396 (1959), Nature, New Biology (1971) 230, p 52)).

Similarly, any of tyrosine alone, derivatives thereof, and salts thereof can be used. Natural tyrosine, synthetic tyrosine, or tyrosine produced by gene recombination can be used. Similarly, any of cysteine alone, derivatives thereof, and salts thereof can be used, including cystine, which is a dimmer of cysteine. Natural cysteine, synthetic cysteine, or cysteine produced by gene recombination can be used. The concentration of tyrosine in the culture solution is 1 mM or higher and/or the concentration of cysteine is at a concentration of the cysteine in the initial medium or higher at least during a predetermined period during the culture.

In the case of employing the fed-batch culture as the method of culturing cells in the present invention, serine and tyrosine and/or cysteine are dissolved at high concentrations to be enriched in a fed-batch medium and a fed-batch medium is added either continuously or sequentially during the culture so that the concentrations of these amino acids are maintained at predetermined concentrations or higher. Specifically, for example a fed-batch medium comprising L-serine at a concentration of about 10-1000 mM, preferably 20-500 mM, more preferably 50-200 mM, may be used as the fed-batch medium. Alternatively, a fed-batch medium comprising L-tyrosine at a concentration of about 0.01-1000 mM, preferably 1-200 mM, more preferably 10-100 mM, or a fed-batch medium comprising L-cysteine hydrochloride monohydrate at a concentration of about 0.01-500 mM, preferably 0.1-50 mM, more preferably 1-10 mM, may be used as the fed-batch medium.

In the case in which the fed-batch medium is added to the culture solution in the present invention, an amount of the fed-batch medium to be added sequentially or continuously over a culture period or for a certain period during the culture period may be 1-150%, preferably 5-50%, more preferably 8-20%, of an amount of the initial medium.

In the present invention, a period of the addition of the fed-batch medium to the culture solution includes at least a part of or an entire period from the start point to the end point of the cell growth phase of the culture. A preferred period is a period from at least 4 days after the start point of the exponential growth phase (normally around day 3 of the culture) of the cells being cultured, preferably from 3 days after the start point of the exponential growth phase, more preferably from the start point of the exponential growth phase (normally around day 3 of the culture). It is preferable to start feeding at least within 3 days from a time when the concentration of the amino acid in the culture solution reaches a predetermined concentration or lower, preferably within 1 day, most preferably before the concentration of the amino acid reaches the predetermined concentration. In the cases in which the culture period is not longer than two weeks, the feeding may be carried out or continued at least until 5 days before the end of the culture, preferably 4 days before, more preferably 3 days before. In the cases in which the culture period is longer than two weeks, the feeding may be carried out or continued at least until the tenth day of the culture, preferably until 5 days before the end of the culture, more preferably until 4 days before the end of the culture, even more preferably until 3 days before the end of the culture.

Components that are commonly used in media for culturing cells (preferably animal cells) can be appropriately used as other components in the culture solution for use in the methods of the present invention, including amino acids, vitamins, lipid factors, energy sources, osmoregulators, iron sources, and pH buffers. In addition to the foregoing components, a minor metal element, surfactant, growth cofactor, nucleoside, or the like may be added. Medium components, including characteristic components, for use in the present invention may be divided, and they may be added separately to be used in the cell culture. Specifically, for instance a high concentration of serine alone and medium components may be used in the cell culture either at the same time or at different times.

Specific examples of the other components in the culture solution include: amino acids such as L-alanine, L-arginine, L-asparagine, L-aspartic acid, L-glutamine, L-glutamic acid, glycin, L-histidine, L-isoleucine, L-leucine, L-lysine, L-methionine, L-ornithine, L-phenylalanine, L-proline, L-threonine, L-tryptophan, and L-valine, preferably L-alanine, L-arginine, L-asparagine, L-aspartic acid, L-glutamine, L-glutamic acid, glycin, L-histidine, L-isoleucine, L-leucine, L-lysine, L-methionine, L-phenylalanine, L-proline, L-threonine, L-tryptophan, and L-valine; vitamins such as I-inositol, biotin, folic acid, lipoic acid, nicotinamide, nicotinic acid, p-aminobenzoic acid, calcium pantothenate, pyridoxal hydrochloride, pyridoxine hydrochloride, riboflavin, thiamine hydrochloride, vitamin B12, and ascorbic acid, preferably biotin, folic acid, lipoic acid, nicotinamide, calcium pantothenate, pyridoxal hydrochloride, riboflavin, thiamine hydrochloride, vitamin B12, and ascorbic acid; lipid factors such as choline chloride, choline tartrate, linoleic acid, oleic acid, and cholesterol, preferably choline chloride; energy sources such as glucose, galactose, mannose, and fructose, preferably glucose; osmoregulators such as sodium chloride, potassium chloride, and potassium nitrate, preferably sodium chloride; iron sources such as iron EDTA, iron citrate, ferrous chloride, ferric chloride, ferrous sulfate, ferric sulfate, and ferric nitrate, preferably ferric chloride, iron EDTA, and iron citrate; and pH buffers such as sodium bicarbonate, calcium chloride, sodium dihydrogen phosphate, HEPES, and MOPS, preferably sodium bicarbonate.

In addition to the components above, the culture solution can comprise, for example, minor metal elements such as copper sulfate, manganese sulfate, zinc sulfate, magnesium sulfate, nickel chlorid, tin chloride, magnesium chloride, and sodium silicite, preferably copper sulfate, zinc sulfate, and magnesium sulfate; surfactants such as Tween 80 and Pluronic F68; and growth cofactors such as recombinant insulin, recombinant IGF, recombinant EGF, recombinant FGF, recombinant PDGF, recombinant TGF-alpha, ethanolamine hydrochloride, sodium selenite, retinoic acid, and putrescine hydrochloride, preferably sodium selenite, ethanolamine hydrochloride, recombinant IGF, and putrescine hydrochloride; and nucleosides such as deoxyadenosine, deoxycytidine, deoxyguanosine, adenosine, cytidine, guanosine, and uridine. In preferred examples of the present invention described above, antibiotics, such as streptomycin, penicillin G potassium, and gentamicin, and pH indicators, such as phenol red, may be contained.

The amount of other components in the culture solution are normally in the ranges of suitably 0.05-1500 mg/L amino acid, 0.001-10 mg/L vitamins, 0-200 mg/L lipid factors, 1-20 g/L energy sources, 0.1-10000 mg/L osmoregulators, 0.1-500 mg/L iron source, 1-10000 mg/L pH buffers, 0.00001-200 mg/L minor metal elements, 0-5000 mg/L surfactant, 0.05-10000 μg/L growth cofactors, and 0.001-50 mg/L nucleosides, but are not limited to these ranges and can be appropriately determined depending on the type of the cell cultured, the type of the desired protein, and the like.

The pH of the culture solution depends on the cells to be cultured, but normally is pH 6.8-7.6, and may often suitably be pH 7.0-7.4.

In the present invention, cells can be cultured using a complete synthetic medium in which the foregoing components are dissolved. It is also possible to use as a basal medium a conventionally known animal cell culture medium, and the medium may be supplemented with the characteristic components for use in the present invention. Examples of commercially-available basal media that can be used as the animal cell culture medium include: D-MEM (Dulbecco's Modified Eagle Medium), D-MEM/F-12 1:1 Mixture (Dulbecco's Modified Eagle Medium: Nutrient Mixture F-12), RPMI1640, CHO-S-SFMII (Invitrogen), CHO-SF (Sigma-Aldrich), EX-CELL 301 (JRH biosciences), CD-CHO (Invitrogen), IS CHO-V (Irvine Scientific), and PF-ACF-CHO (Sigma-Aldrich). In cases of culturing cells by fed-batch culture, such commercially-available media can be used as the initial medium at an early stage of the cell culture. The same medium as used as the initial medium may be concentrated and supplemented with serine and tyrosine and/or cysteine and then used as the fed-batch medium.

The culture methods of the present invention can be used to culture various cells (e.g., bacterial cells, fungal cells, insect cells, plant cells, animal cells) without any limitation. For example, recombinant COS cells or recombinant CHO cells carrying a gene encoding a desired protein prepared by genetic engineering, or fused cells producing antibodies, exemplified by hybridoma such as mouse-human, mouse-mouse, and mouse-rat, can be cultured. The methods of the present invention can be used to culture animal cells to obtain natural type proteins that the animal cells produce, or to culture BHK cells, HeLa cells, and the like as well as the cells described above.

Especially preferred animal cells in the present invention are CHO cells in to which a gene encoding a desired protein is introduced. The desired protein is not particularly limited and may be any protein such as antibodies, such as natural antibodies, antibody fragments, small antibody fragments or "minibody", chimeric antibodies, and humanized antibodies (e.g., anti-IL-6 receptor antibodies, anti-glypican-3 antibodies, anti-CD3 antibodies, anti-CD20 antibodies, anti-GPIIb/IIIa antibodies, anti-TNF antibodies, anti-CD25 antibodies, anti-EGFR antibodies, anti-Her2/neu antibodies, anti-RSV antibodies, anti-CD33 antibodies, anti-CD52 antibodies, anti-IgE antibodies, anti-CD11a antibodies, anti-VEGF antibodies, anti-VLA4 antibodies) and physiologically active proteins (e.g., granulocyte colony-stimulating factor (G-CSF), granulocyte macrophage colony-stimulating factor (GM-CSF), erythropoietin, interferon, interleukin such as IL-1 and IL-6, t-PA, urokinase, serum albumin, blood coagulation factor), but antibodies are especially preferred.

Antibodies produced by the methods of the present invention include not only monoclonal antibodies derived from animals, such as human, mouse, rat, hamster, rabbit, and monkey, but also artificially-modified gene recombinant antibodies, such as chimeric antibodies, humanized antibodies, and bispecific antibodies. The immunoglobulin class of an antibody is not particularly limited, and may be any of IgG, such as IgG1, IgG2, IgG3, and IgG4, IgA, IgD, IgE, and IgM, but IgG and IgM are preferred in pharmaceutical uses. The antibodies of the present invention include not only whole antibodies but also antibody fragments, such as Fv, Fab, and F(ab)$_2$, and minibodies which are single chain Fv (e.g., scFv, sc(Fv)$_2$) with uni-, bi- or multi-valent binding in which variable regions of the antibodies are connected by linkers such as peptide linkers.

Since culture conditions differ according to types of cells to be used, suitable conditions can be appropriately determined. For example, CHO cells may be cultured, normally, in an atmosphere of $CO_2$ gas at a concentration of 0-40%, preferably 2-10%, at 30-39° C., preferably about 37° C., for 1-50 days, preferably 1-14 days.

Various bioreactors for animal cell cultures can be used; for example, fermenter-type tank bioreactors, airlift bioreactors, culture flask bioreactors, spinner flask bioreactors, microcarrier bioreactors, fluidized-bed bioreactors, hollow fiber bioreactors, roller bottle bioreactors, and packed-bed bioreactors.

Culturing cells (preferably animal cells) by the methods of the present invention enables high-yield production of proteins.

Some proteins can be produced merely by culturing cells that produce the proteins, while production of some other proteins requires a special operation. The operation or conditions may be appropriately determined according to animal cells to be cultured. For example, in the case of CHO cells transformed by genetic engineering with a vector having a gene encoding a mouse-human chimeric antibody, the cells may be cultured under the foregoing conditions so that a desired protein is obtained in the medium within 1-50 days, preferably 5-21 days, more preferably about 7-14 days. The resulting protein may be isolated and purified by methods well known in the art (refer to, for example, *Kotaikogakunyumon* (Introduction to Antibody Engineering), Chijinshokan Co. Ltd., (1994) p. 102-104; Affinity Chromatography Principles & Methods, GE Healthcare, (2003) p. 56-60) to obtain the desired protein.

The present invention enables high-yield production of recombinant antibodies (e.g., natural antibodies, antibody fragments, fragmented antibodies, chimeric antibodies, humanized antibodies, bispecific antibodies), gene recombinant proteins (e.g., granulocyte colony-stimulating factors (G-CSF), granulocyte macrophage colony-stimulating factors (GM-CSF), erythropoietins, interferon, interleukin, such as IL-1 and IL-6, t-PA, urokinase, serum albumin, blood coagulation factors), and the like.

In cases in which a protein or polypeptide produced by the methods of the present invention (the protein and the polypeptide are sometimes referred to as the protein of the present invention) has a biological activity that can be utilized as a pharmaceutical, such a protein or polypeptide may be mixed with a pharmaceutically acceptable carrier or additive and formulated to produce a medicament. Proteins of the present invention, and medicaments comprising as an active ingredient the proteins of the present invention are also encompassed within the scope of the present invention.

Examples of pharmaceutically acceptable carriers and additives include water, pharmaceutically acceptable organic solvents, collagen, polyvinyl alcohol, polyvinyl pyrrolidone, carboxyvinyl polymer, sodium carboxymethyl cellulose, sodium polyacrylate, sodium alginate, water-soluble dextran, sodium carboxymethyl starch, pectin, methyl cellulose, ethyl cellulose, xanthan gum, gum arabic, casein, agar, polyethylene glycol, diglycerol, glycerol, propylene glycol, Vaseline, paraffin, stearyl alcohol, stearic acid, human serum albumin (HSA), mannitol, sorbitol, lactose, and surfactants that are acceptable as pharmaceutical additives.

An actual additive is selected from the foregoing, either alone or in combination, according to a form of a therapeutic agent that is a pharmaceutical of the present invention, but is definitely not limited to those listed above. For example, in cases of using as a formulation for injection, an additive prepared by dissolving a purified polypeptide into a solvent, such as physiological saline, a buffer solution, and a grape sugar solution, and adding an adsorption preventive agent, such as Tween 80, Tween 20, gelatin, and human serum albumin, may be used. A freeze-dried additive may be used to realize a form that dissolves and restructures before use, and for example sugar alcohols and sugars, such as mannitol and grape sugar, may be used as excipients for freeze drying.

An effective amount of administration of the polypeptide is appropriately selected according to a type of the polypeptide, a type of disease to be treated or prevented, an age of a patient, severity of disease, and the like. For instance, in cases in which the protein of the present invention is an antibody, such as an anti-glypican antibody, the effective amount of administration is selected from the range of 0.001 mg to 1000 mg per one kilogram of body weight per administration. The amount of administration can be selected from the range of 0.01 to 100000 mg/body of a patient. The amount of administration, however, is not limited to the foregoing.

Methods of administration of pharmaceuticals of the present invention may be either of oral administration and parenteral administration, but parenteral administration is preferred; specific examples include injection (e.g., general or local administration by intravenous injection, intramuscular injection, intraperitoneal injection, subcutaneous injection, or the like), transnasal administration, lung administration, and percutaneous administration.

EXAMPLES

The present invention is described in detail below, with reference to the Examples and Reference Examples. The following Examples and the like illustrate the present invention without, however, limiting the present invention thereto.

[Example 1] Fed-Batch Culture Using a Fed-Batch Medium Comprising Serine, Cysteine, and Tyrosine at High Concentrations and Having a Low pH (a CHO Cell Strain Transformed with an Antibody Gene)

A composition of a medium and a method of preparation are as follows.

Initial medium: A commercially-available animal cell culture medium was dissolved and then sterilized by filtration.

Fed-batch medium: An animal cell culture medium for use in the initial medium was dissolved such that a concentration of the animal cell culture medium was three times the concentration of the initial medium. Then, 50 mM of serine, 1.8 mM of cysteine hydrochloride monohydrate, and 14.5 mM of tyrosine were added, and a pH was decreased with hydrochloric acid until the medium components were completely dissolved (around pH 1.5). After it was confirmed that the medium components were completely dissolved, the resulting medium was sterilized by filtration.

Cells: Humanized IgG (anti-glypican-3 antibody)-producing CHO cell strain (refer to WO 2006/006693 pamphlet).

Figure 2:
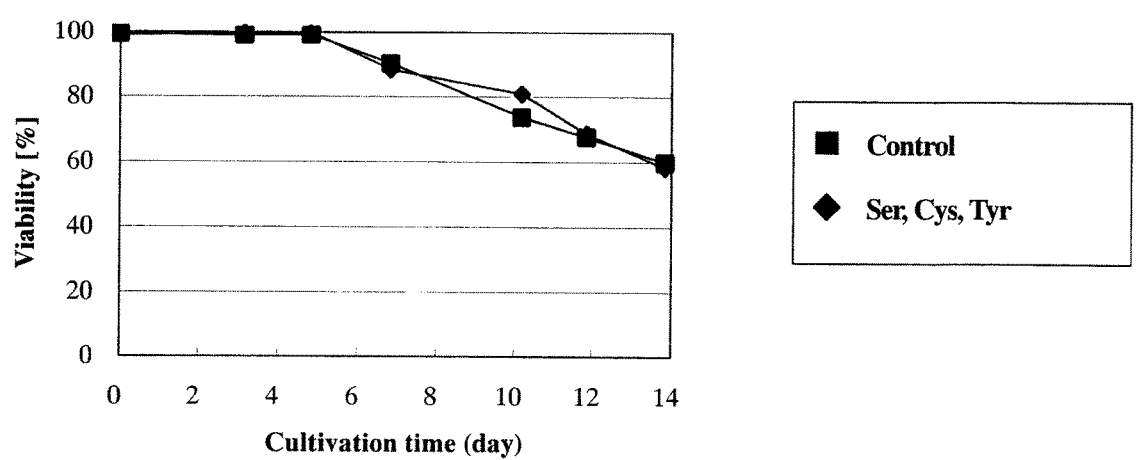
FIG. 2 shows the transition of viability during the culture period. (Example 1)
Figure 3:
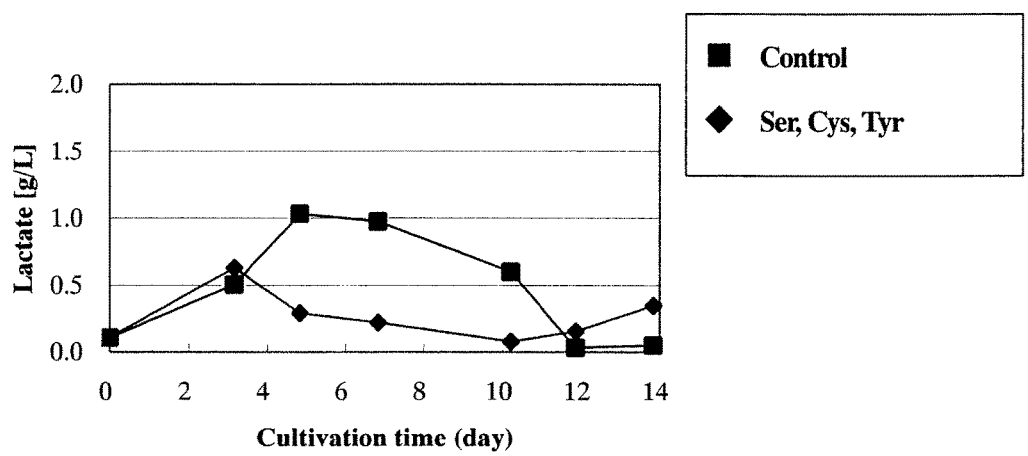
FIG. 3 shows the transition of concentrations of lactate during the culture period. (Example 1)

The initial medium was charged into a jar-type cell culture apparatus, and the CHO cells were added so as to be $2\times10^5$ cells/mL to start cultivation under conditions of 37° C. and 10% $CO_2$. During a 14-day culture period, a lower limit of the pH was automatically controlled to 7.0, and a concentration of dissolved oxygen was automatically controlled to 40%. From the third day of the culture, the fed-batch medium was fed at a constant flow rate (1.0 g/hour with respect to 1 L initial medium), and the cultivation was continued until the fourteenth day. Sampling was carried out at the beginning of the cultivation and on the third, fifth, seventh, tenth, twelfth, and fourteenth days. Culture supernatants of the respective samples were subjected to affinity chromatography using protein A to measure concentrations of antibodies that were produced, subjected to trypan blue staining to measure survival rates, and subjected to immobilized enzyme method to quantitate lactate. As shown in FIG. 1, in the case of the fed-batch culture (Control) using the fed-batch medium that was not enriched with serine, cysteine, and tyrosine, the concentration of the antibody that was obtained as a result of the 14-day culture was about 1.6 g/L. On the other hand, in the case of the fed-batch culture (Ser, Cys, Tyr) using the fed-batch medium having a low pH and comprising increased amounts of serine, cysteine, and tyrosine at high concentrations, the concentration of antibody that was obtained as a result of the 14-day culture was about 2.2 g/L; the concentration was higher by about 40%. FIG. 2 shows the transition of viability (survival rates) during the culture period. Further, as shown in FIG. 3, the concentration of lactate transitioned at a low level from the third day of the culture in the fed-batch culture using the fed-batch medium having a low pH and enriched with serine, cysteine, and tyrosine, as compared to the fed-batch culture using the fed-batch medium that was not enriched with serine, cysteine, and tyrosine.

[Example 2] Fed-Batch Culture Using a Fed-Batch Medium Comprising Serine, Cysteine, and Tyrosine at High Concentrations and Having a Low pH (a CHO Cell Strain Transformed with an Antibody Gene and Hamster Taurine Transporter Gene)

A composition of a medium and a method of preparation are as follows.

Initial medium: A commercially-available animal cell culture medium was dissolved and then sterilized by filtration.

Fed-batch medium: An animal cell culture medium for use in the initial medium was dissolved such that a concentration of the animal cell culture medium was three times the concentration of the initial medium. Then, 50 mM of serine, 1.8 mM of cysteine hydrochloride monohydrate, and 14.5 mM of tyrosine were added, and a pH was decreased with hydrochloric acid until the medium components were completely dissolved (around pH 1.5). After it was confirmed that the medium components were completely dissolved, the resulting medium was sterilized by filtration.

Cells: Humanized IgG-producing CHO cell strain transformed with a taurine transporter gene.

Figure 4:
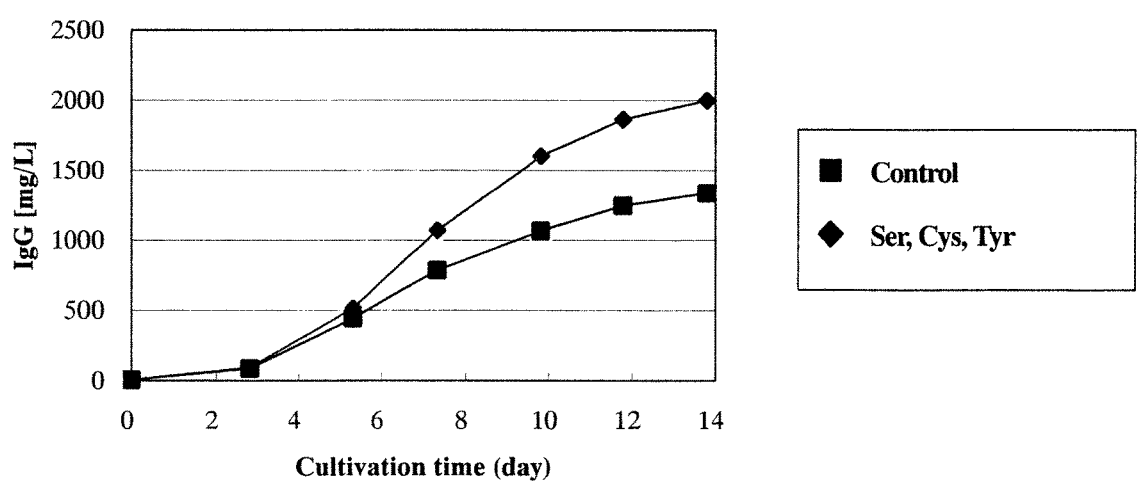
FIG. 4 shows the transition of concentrations of antibodies during the culture period. (Example 2)
Figure 5:
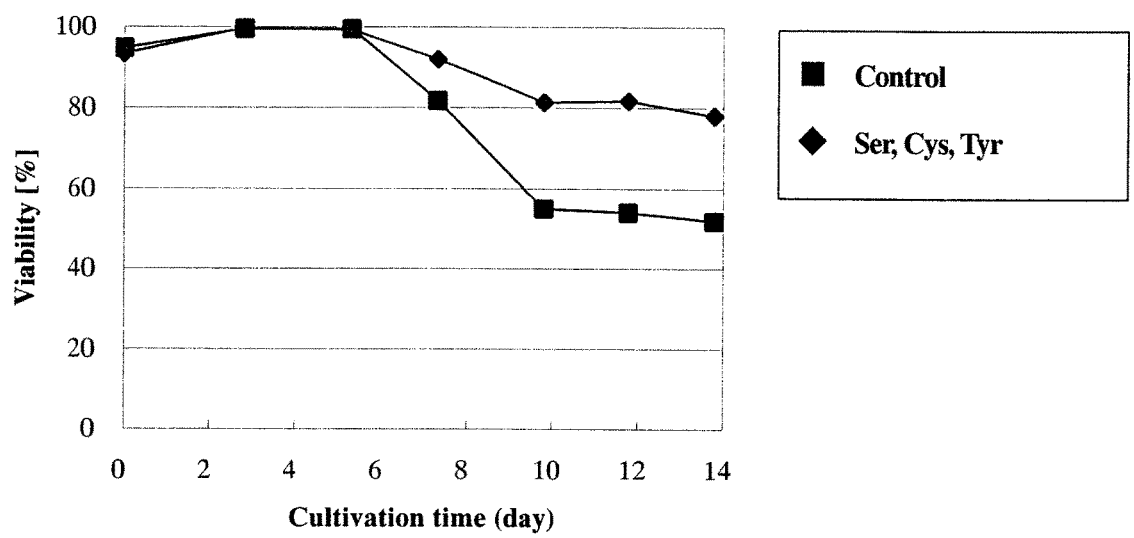
FIG. 5 shows the transition of viability during the culture period. (Example 2)
Figure 6:
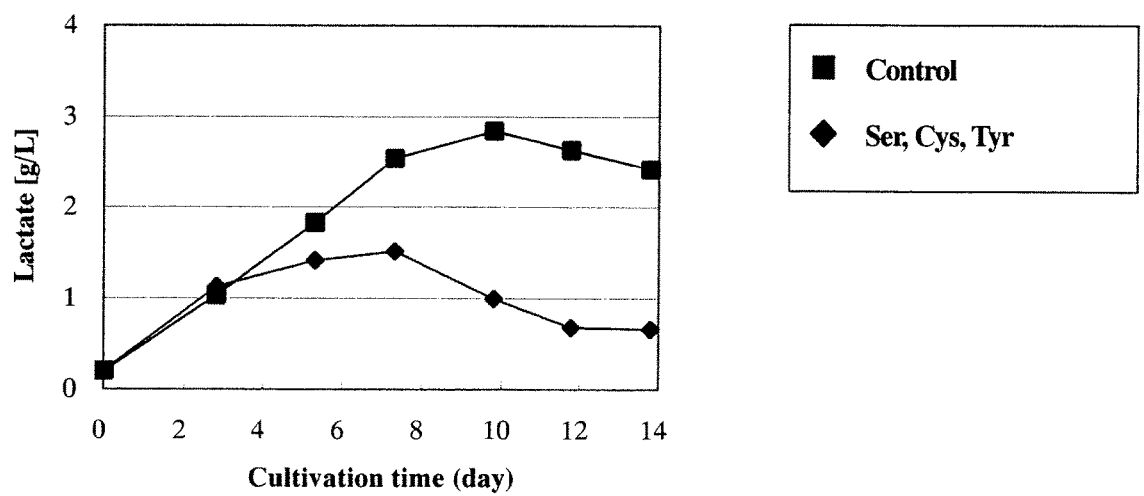
FIG. 6 shows the transition of concentrations of lactate during the culture period. (Example 2)

The initial medium was charged into a jar-type cell culture apparatus, and the CHO cells were added so as to be $2\times10^5$ cells/mL to start cultivation under conditions of 37° C. and 10% $CO_2$. During a 14-day culture period, a lower limit of the pH was automatically controlled to 7.0, and a concentration of dissolved oxygen was automatically controlled to 40%. From the third day of the culture, the fed-batch medium was fed at a constant flow rate (1.5 g/hour with respect to 1 L initial medium), and the culture was continued until the fourteenth day. Sampling was carried out at the beginning of the culture and on the third, fifth, seventh, twelfth, and fourteenth days. Culture supernatants of the respective samples were subjected to affinity chromatography using protein A to measure concentrations of antibodies that were produced, subjected to trypan blue staining to measure survival rates, and subjected to immobilized enzyme method to quantitate lactate. As shown in FIG. 4, in the case of the fed-batch culture (Control) using the fed-batch medium that was not enriched with serine, cysteine, and tyrosine, the concentration of the antibody that was obtained as a result of the 14-day culture was about 1.3 g/L. On the other hand, in the case of the fed-batch culture (Ser, Cys, Tyr) using the fed-batch medium comprising increased amounts of serine, cysteine, and tyrosine at high concentrations and having a low pH, the concentration of the antibody that was obtained as a result of the 14-day culture was about 2.0 g/L; the concentration was higher by about 54%. As shown in FIG. 5, in the case of the fed-batch culture using the fed-batch medium that was not enriched with serine, cysteine, and tyrosine, the survival rate was 52% on the fourteenth day of the 14-day culture. On the other hand, in the case of the fed-batch culture using the fed-batch medium having a low pH and comprising increased amounts of serine, cysteine, and tyrosine at high concentrations, the survival rate was 78% on the fourteenth day of the 14-day culture; a high viability was maintained. Further, as shown in FIG. 6, the concentration of lactate transitioned at a low level from the third day of the culture in the fed-batch culture using the fed-batch medium having a low pH and enriched with serine, cysteine, and tyrosine, as compared with the fed-batch culture using the fed-batch medium that was not enriched with serine, cysteine, and tyrosine.

[Example 3] Fed-Batch Culture Showing Contribution of High Concentrations of Serine, Cysteine, and Tyrosine to Achieve High-Yield Production of Antibodies (a CHO Cell Strain Transformed with an Antibody Gene and a Hamster Taurine Transporter Gene)

A composition of a medium and a method of preparation are as follows.

Initial medium: A commercially-available animal cell culture medium was dissolved and then sterilized by filtration.

Fed-batch medium (Ser, Cys, Tyr): An animal cell culture medium for use in the initial medium was dissolved such that a concentration of the animal cell culture medium was three times the concentration of the initial medium. Then, 50 mM of serine, 1.8 mM of cysteine hydrochloride monohydrate, and 14.5 mM of tyrosine were added, and a pH was decreased with hydrochloric acid until the medium components were completely dissolved (around pH 1.5). After it was confirmed that the medium components were completely dissolved, the resulting medium was sterilized by filtration.

Fed-batch medium (Ser, Cys): An animal cell culture medium for use in the initial medium was dissolved such that a concentration of the animal cell culture medium was three times the concentration of the initial medium. Then, 50 mM of serine and 1.8 mM of cysteine hydrochloride monohydrate were added, and a pH was decreased with hydrochloric acid until the medium components were completely dissolved (around pH 1.0). After it was confirmed that the medium components were completely dissolved, the resulting medium was sterilized by filtration.

Fed-batch medium (Ser, Tyr): An animal cell culture medium for use in the initial medium was dissolved such that a concentration of the animal cell culture medium was three times the concentration of the initial medium. Then, 50 mM of serine and 14.5 mM of tyrosine were added, and a pH was decreased with hydrochloric acid until the medium components were completely dissolved (around pH 1.0). After it was confirmed that the medium components were completely dissolved, the resulting medium was sterilized by filtration.

Fed-batch medium (Cys, Tyr): An animal cell culture medium for use in the initial medium was dissolved such that a concentration of the animal cell culture medium was three times the concentration of the initial medium. Then, 1.8 mM of cysteine hydrochloride monohydrate and 14.5 mM of tyrosine were added, and a pH was decreased with hydrochloric acid until the medium components were completely dissolved (around pH 1.0). After it was confirmed that the medium components were completely dissolved, the resulting medium was sterilized by filtration.

Cells: Humanized IgG-producing CHO cell strain transformed with a taurine transporter gene.

Figure 7:
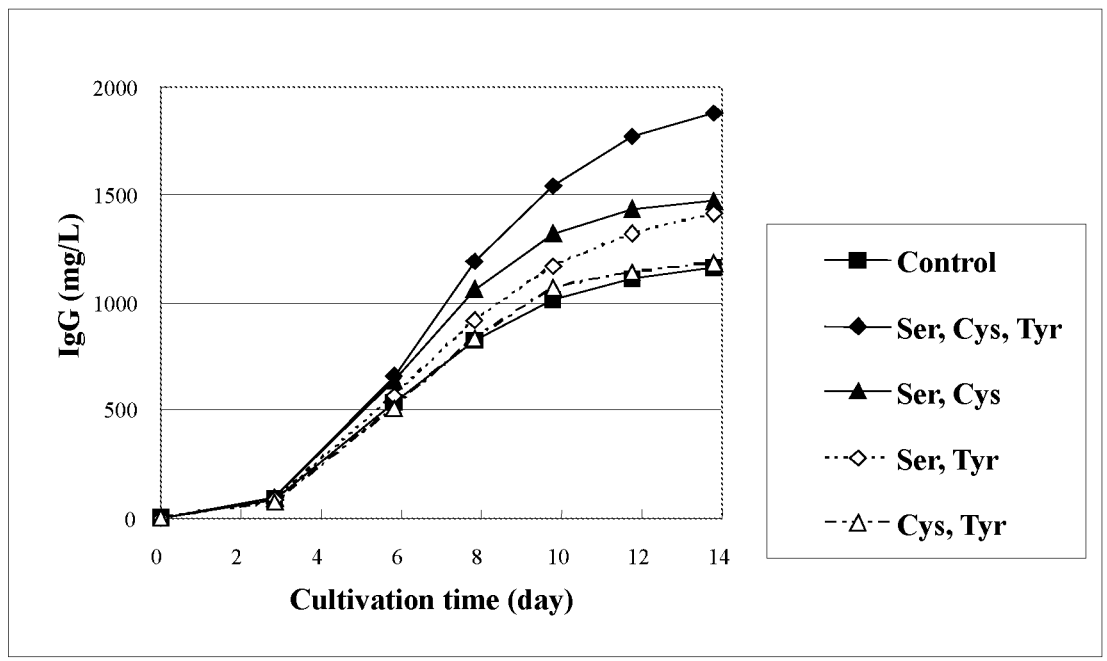
FIG. 7 shows the transition of concentrations of antibodies during the culture period. (Example 3)

The initial medium was charged into a jar-type cell culture apparatus, and the CHO cells were added so as to be $2 \times 10^5$ cells/mL to start cultivation under conditions of 37° C. and 10% $CO_2$. During a 14-day culture period, a lower limit of the pH was automatically controlled to 7.0, and a concentration of dissolved oxygen was automatically controlled to 40%. From the third day of the culture, the fed-batch medium was fed at a constant flow rate (1.0 g/hour with respect to 1 L initial medium), and the culture was continued until the fourteenth day. Sampling was carried out at the beginning of the culture and on the third, fifth, seventh, tenth, twelfth, and fourteenth days. Concentrations of antibodies that were produced in culture supernatants of the respective samples were measured by affinity chromatography using protein A, and concentrations of amino acids, serine and tyrosine, in the culture supernatants of the respective samples were measured by amino acid analysis using an ion exchange column. As shown in FIG. 7, in the case of the fed-batch culture (Control) using the fed-batch medium that was not enriched with serine, cysteine, and tyrosine, the concentration of the antibody that was obtained as a result of the 14-day culture was about 1.16 g/L. On the other hand, in the case of the fed-batch culture (Ser, Cys, Tyr) using the fed-batch medium having a low pH and comprising increased amounts of serine, cysteine, and tyrosine at high concentrations, the concentration of the antibody that was obtained as a result of the 14-day culture was 1.87 g/L; in the case of the fed-batch culture (Ser, Cys) using the fed-batch medium having a low pH and comprising increased amounts of serine and cysteine at high concentrations, the concentration of the antibody that was obtained as a result of the 14-day culture was 1.47 g/L; in the case of the fed-batch culture (Ser, Tyr) using the fed-batch medium having a low pH and comprising increased amounts of serine and tyrosine at high concentrations, the concentration of the antibody that was obtained as a result of the 14-day culture was 1.41 g/L; and in the case of the fed-batch culture (Cys, Tyr) using the fed-batch medium having a low pH and comprising increased amounts of cysteine and tyrosine, the concentration of the antibody that was obtained as a result of the 14-day culture was 1.18 g/L. The results suggest that high concentrations of serine, cysteine, and tyrosine contributed in this order to high-yield production of antibodies. The results also suggest that addition of high concentrations of serine, cysteine, and tyrosine all together to the fed-batch medium in the same instance most significantly contributed to high-yield production of antibodies.

Figure 8:
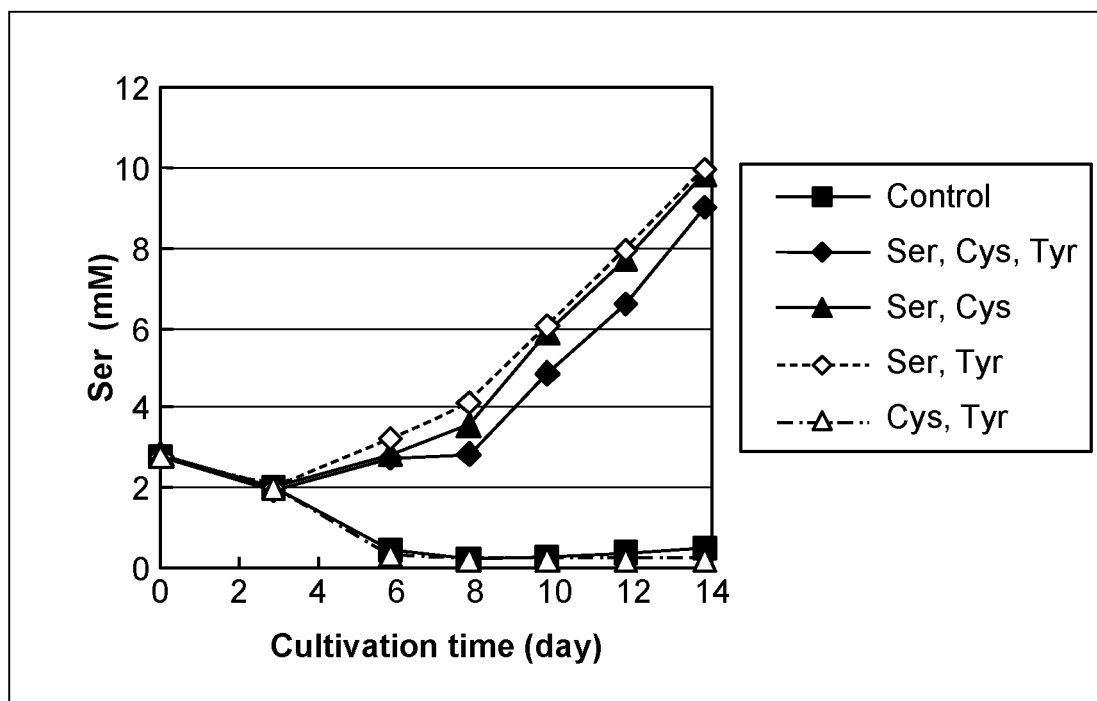
FIG. 8 shows the transition of concentrations of serine during the culture period. (Example 3)

FIGS. 8 and 9 show the transitions of the concentrations of serine and tyrosine during the 14-day culture period. In the control, the concentration of serine was 0.63 mM and the concentration of tyrosine was 0.34 mM on the fifth day, and the concentration of serine was 0.4 mM or lower and the concentration of tyrosine was 0.4 mM or lower from the seventh day of the culture. On the other hand, the concentration of serine was maintained at 2 mM or higher in the culture using the fed-batch medium supplemented with serine, and the concentration of tyrosine was maintained at 1 mM or higher in the culture using the fed-batch medium supplemented with tyrosine.

The following Reference Examples describe the preparation of humanized IgG-producing CHO cell strains transformed with a taurine transporter gene that were used in Examples 2 and 3 described above.

Figure 11:
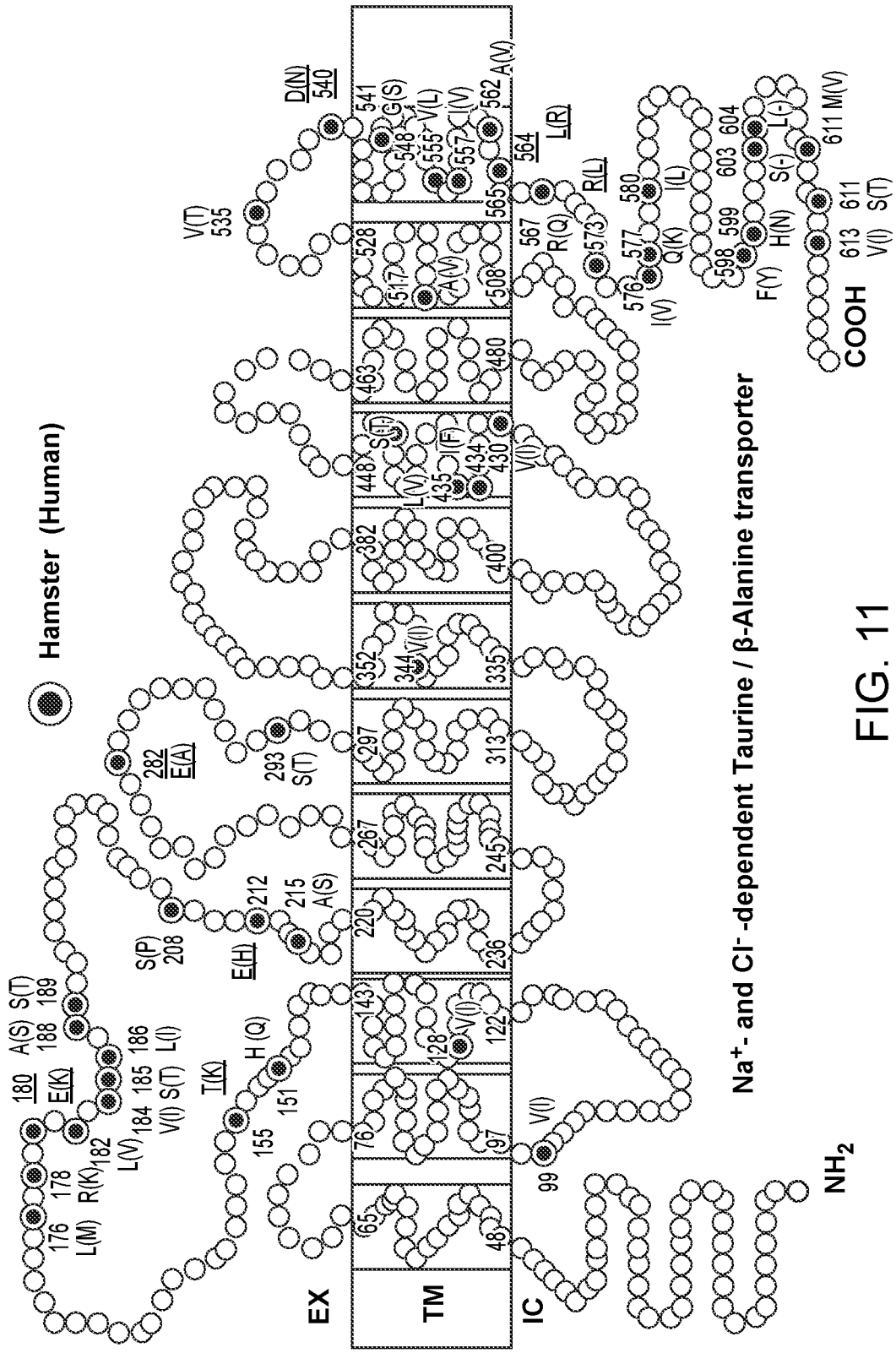
FIG. 11 shows a structure of the hamster taurine transporter. (Reference Example 1)

[Reference Example 1] Cloning of a Hamster Taurine Transporter Gene Derived from CHO Cells Total RNA was extracted from cells producing anti-IL-6 receptor antibody (JP H08-99902 A), obtained by transforming an anti-IL-6 receptor antibody gene into CHO DXB11 cells. Thereafter, polyA-dependent cDNA was synthesized. A hamster taurine transporter (Hamster TauT) gene was obtained by PCR using as a template cDNA fragmented by three types of restriction enzymes, SalI, XhoI, and EcoRI. A PCR primers containing 5', 3' conservative sequences which are common between known Rat/Mouse TauT were designed and used. After nucleotide sequence of the cloned gene was determined, it was confirmed that the gene encoded Hamster TauT, based on homology with known TauT from other biological species (FIG. 10). The amino acid sequence of Hamster TauT was highly homologous with that from Mouse (96% Identity), Rat (96% Identity), and Human (93% Identity); therefore, it was speculated that Hamster TauT was a transporter having 12 trans-membrane domains (FIG. 11).

Figure 12:
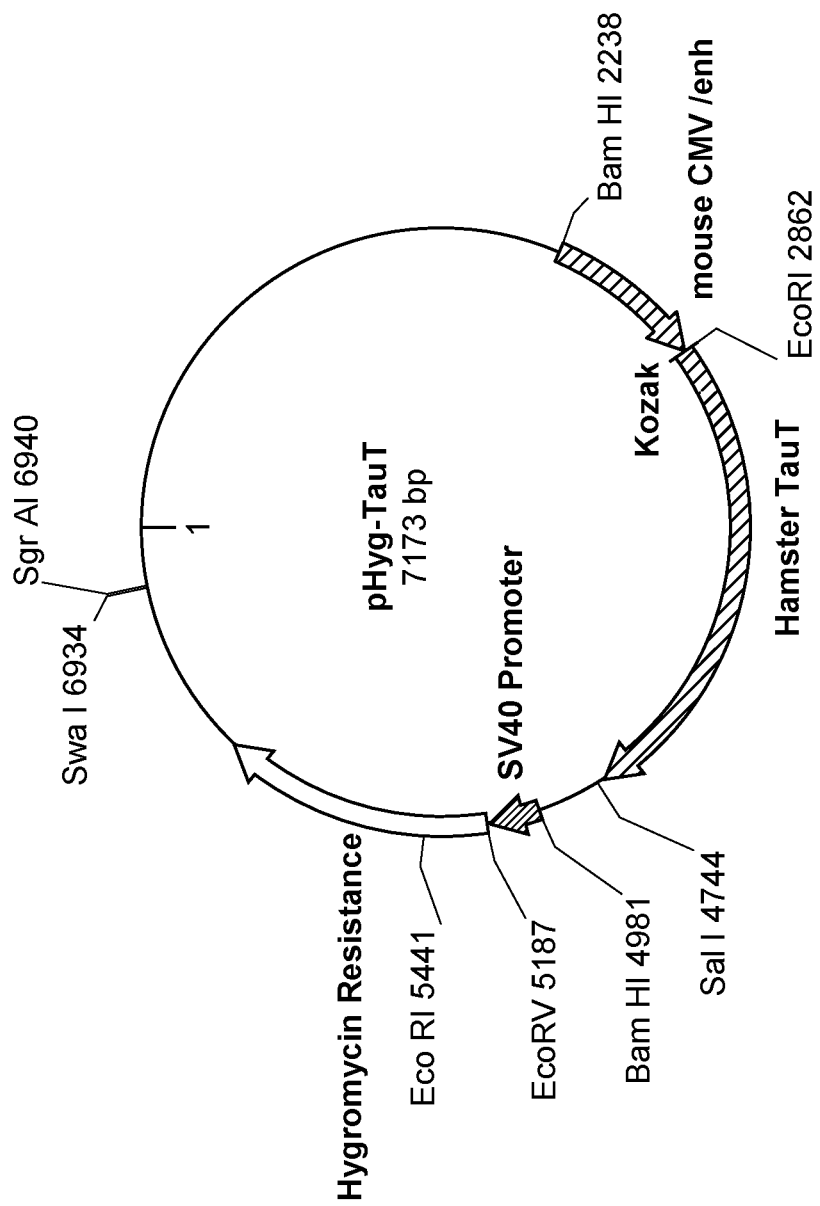
FIG. 12 shows a structure of an expression plasmid pHyg/TauT. (Reference Example 2)

[Reference Example 2] Preparation of CHO Cell Strains into which a Hamster Taurine Transporter Gene is Introduced An expression plasmid pHyg/TauT (FIG. 12) with CMV promoter was constructed by adding a Kozak sequence to the Hamster TauT gene (hereinafter "TauT") obtained by the cloning in Reference Example 1. CHO cells expressing anti-glypican-3 antibody, as the parent strain, (refer to WO 2006/006693 pamphlet), were transformed by electroporation with the plasmid pHyg/TauT or a control plasmid pHyg without TauT. Cells transformed with the expression plasmid were selected in the presence of Hygromycin (400 μg/ml), followed by expansion of all cell strains showing stable growth (pHyg/TauT: 8 strains, pHyg: 7 strains). After TauT mRNA was prepared, the TaqMan procedure was performed to select 7 strains showing superior expression over the parent strain to obtain cells transformed with pHyg/TauT. An average amount of mRNA expression of the transformed cells (7 strains) was about 40-fold the control (7 strains).

Free Text of Sequence List
<SEQ ID NO: 1> SEQ ID NO: 1 shows the base sequence of a gene encoding a hamster taurine transporter.
<SEQ ID NO: 2> SEQ ID NO: 2 shows the amino acid sequence of a hamster taurine transporter.

The invention claimed is:

1. A method of producing an antibody by culturing a CHO cell by fed-batch culture, comprising culturing a CHO cell, which is transformed with a gene of an antibody and with a hamster taurine transporter gene, in a culture solution comprising an initial medium and adding a fed-batch medium to the culture solution during the culturing, wherein the fed-batch medium is enriched with
serine, tyrosine and cysteine
wherein said adding results in feeding serine, tyrosine and cysteine to the culture solution and maintaining in the culturing solution a concentration of serine at 2 mM or higher and a concentration of tyrosine at 1 mM or higher from a fourth day to a tenth day of the culturing,
wherein the culturing results in producing the antibody,
wherein the fed-batch medium is prepared by adding only three amino acids, which are serine, tyrosine, and cysteine, to a medium, which has the same composition as the initial medium and a concentration of each of serine, tyrosine, and cysteine in the fed-batch medium is higher than a respective concentration in the initial medium,
wherein the concentration of serine in the fed-batch medium is of 10 mM to 1000 mM, and
wherein the fed-batch medium is fed at a constant flow rate beginning on a third day of the culturing and extending to an end of the culturing.

2. The method of claim 1, wherein the concentration of serine, tyrosine and cysteine is maintained in the culture solution during an entire culture period.

3. The method according to claim 1, wherein the concentration of tyrosine in the fed-batch medium is from 10 mM to 100 mM, and the concentration of cysteine in the fed-batch medium is from 1 mM to 10 mM.

4. The method of claim 1, wherein the concentration of serine and tyrosine is maintained in the culture solution from a third day to the tenth day of the culturing.

5. The method of claim 1, wherein the antibody is an anti-glypican-3 antibody.

6. The method of claim 1, wherein a concentration of the produced antibody is higher than a concentration of the antibody produced using a fed-batch medium that is not enriched with serine, cysteine and tyrosine.

* * * * *

```
                              SEQUENCE LISTING

<160> NUMBER OF SEQ ID NOS: 2

<210> SEQ ID NO 1
<211> LENGTH: 1869
<212> TYPE: DNA
<213> ORGANISM: Cricetulus griseus
<220> FEATURE:
<221> NAME/KEY: CDS
<222> LOCATION: (1)..(1866)

<400> SEQUENCE: 1 atg gcc acc aag gag aag ctg cag tgt ctg aaa gac ttc cac aaa gac      48
Met Ala Thr Lys Glu Lys Leu Gln Cys Leu Lys Asp Phe His Lys Asp
1               5                  10                  15 atc ctg aag cct tct cca ggg aag agc cca ggc aca cgg cct gag gat      96
Ile Leu Lys Pro Ser Pro Gly Lys Ser Pro Gly Thr Arg Pro Glu Asp
            20                  25                  30 gag gct gag ggg aag ccc cct cag agg gag aag tgg tcc agc aag att     144
Glu Ala Glu Gly Lys Pro Pro Gln Arg Glu Lys Trp Ser Ser Lys Ile
        35                  40                  45 gac ttt gtg ctg tct gtg gcc gga ggc ttc gtg ggt ttg ggc aac gtt     192
Asp Phe Val Leu Ser Val Ala Gly Gly Phe Val Gly Leu Gly Asn Val
    50                  55                  60 tgg cgt ttc ccg tac ctc tgc tac aaa aat ggt gga ggt gct ttc ctc     240
Trp Arg Phe Pro Tyr Leu Cys Tyr Lys Asn Gly Gly Gly Ala Phe Leu
65                  70                  75                  80 ata ccg tat ttt att ttc ctg ttt ggg agt ggc ctg cct gtg ttt ttc     288
Ile Pro Tyr Phe Ile Phe Leu Phe Gly Ser Gly Leu Pro Val Phe Phe
                85                  90                  95 ctg gag gtc ata ata ggc cag tac acc tca gaa ggg gga atc acc tgc     336
Leu Glu Val Ile Ile Gly Gln Tyr Thr Ser Glu Gly Gly Ile Thr Cys
            100                 105                 110 tgg gag aag atc tgc ccc ttg ttc tct ggc att ggc tac gca tcc atc     384
Trp Glu Lys Ile Cys Pro Leu Phe Ser Gly Ile Gly Tyr Ala Ser Ile
        115                 120                 125 gtc atc gtg tcc ctc ctg aat gtg tac tac att gtc atc ctg gcc tgg     432
Val Ile Val Ser Leu Leu Asn Val Tyr Tyr Ile Val Ile Leu Ala Trp
    130                 135                 140 gcc aca tac tac cta ttt cac tcc ttc cag aca gag ctt ccc tgg gcc     480
Ala Thr Tyr Tyr Leu Phe His Ser Phe Gln Thr Glu Leu Pro Trp Ala
145                 150                 155                 160 cac tgc aac cac agc tgg aac aca cca cat tgc atg gag gac acc ctg     528
His Cys Asn His Ser Trp Asn Thr Pro His Cys Met Glu Asp Thr Leu
                165                 170                 175 cgt agg aat gag agt ctc tgg gtc tcc ctt agc gcc tcc aac ttc acc     576
Arg Arg Asn Glu Ser Leu Trp Val Ser Leu Ser Ala Ser Asn Phe Thr
            180                 185                 190 tcg cct gtc atc gag ttc tgg gag cgc aat gta ctc agc ctg tct tcc     624
Ser Pro Val Ile Glu Phe Trp Glu Arg Asn Val Leu Ser Leu Ser Ser
        195                 200                 205 gga atc gac gaa cca ggc gct ctg aaa tgg gac ctt gcg ctc tgc ctc     672
Gly Ile Asp Glu Pro Gly Ala Leu Lys Trp Asp Leu Ala Leu Cys Leu
    210                 215                 220 ctc tta gtc tgg ctt gtc tgt ttt ttc tgc ata tgg aag ggt gtt cga     720
Leu Leu Val Trp Leu Val Cys Phe Phe Cys Ile Trp Lys Gly Val Arg
225                 230                 235                 240
```

|  |  |
|---|---|
| tcc aca ggc aag gtt gtc tac ttc acc gcc act ttc ccg ttt gcc atg<br>Ser Thr Gly Lys Val Val Tyr Phe Thr Ala Thr Phe Pro Phe Ala Met<br>                 245                            250                    255 | 768 |
| ctt ctg gtg ctg ctg gtc cgt gga ctg acc ctg ccg ggt gct ggc gaa<br>Leu Leu Val Leu Leu Val Arg Gly Leu Thr Leu Pro Gly Ala Gly Glu<br>                260                         265                    270 | 816 |
| ggc atc aaa ttc tac ctg tac cct gac atc agc cgc ctt gag gac cca<br>Gly Ile Lys Phe Tyr Leu Tyr Pro Asp Ile Ser Arg Leu Glu Asp Pro<br>        275                        280                    285 | 864 |
| cag gtg tgg atc gac gcc gga acc cag ata ttc ttt tcc tat gcc atc<br>Gln Val Trp Ile Asp Ala Gly Thr Gln Ile Phe Phe Ser Tyr Ala Ile<br>             290                         295                    300 | 912 |
| tgc ctg ggg gcc atg acc tca ctg gga agc tac aac aag tac aag tat<br>Cys Leu Gly Ala Met Thr Ser Leu Gly Ser Tyr Asn Lys Tyr Lys Tyr<br>305                        310                    315                  320 | 960 |
| aac tcg tac agg gac tgt atg ctg ctg gga tgc ctg aac agt ggt acc<br>Asn Ser Tyr Arg Asp Cys Met Leu Leu Gly Cys Leu Asn Ser Gly Thr<br>                325                         330                    335 | 1008 |
| agt ttt gtg tct ggc ttc gca gtt ttt tcc atc ctg ggc ttc atg gca<br>Ser Phe Val Ser Gly Phe Ala Val Phe Ser Ile Leu Gly Phe Met Ala<br>                  340                         345                    350 | 1056 |
| caa gag caa ggg gtg gac att gct gat gtg gct gag tca ggt cct ggc<br>Gln Glu Gln Gly Val Asp Ile Ala Asp Val Ala Glu Ser Gly Pro Gly<br>            355                         360                    365 | 1104 |
| ttg gcc ttc att gcc tat cca aaa gct gtg act atg atg ccg ctg ccc<br>Leu Ala Phe Ile Ala Tyr Pro Lys Ala Val Thr Met Met Pro Leu Pro<br>370                        375                    380 | 1152 |
| acc ttt tgg tcc att ctg ttt ttt att atg ctc ctc ttg ctt gga ctg<br>Thr Phe Trp Ser Ile Leu Phe Phe Ile Met Leu Leu Leu Leu Gly Leu<br>385                        390                    395                  400 | 1200 |
| gac agc cag ttt gtt gaa gtc gaa gga cag atc aca tcc ttg gtt gat<br>Asp Ser Gln Phe Val Glu Val Glu Gly Gln Ile Thr Ser Leu Val Asp<br>                  405                         410                    415 | 1248 |
| ctt tac ccg tcc ttc cta agg aag ggt tat cgt cgg gaa gtc ttc atc<br>Leu Tyr Pro Ser Phe Leu Arg Lys Gly Tyr Arg Arg Glu Val Phe Ile<br>            420                         425                    430 | 1296 |
| gcc atc ctg tgt agc atc agc tac ctg ctg ggg ctg tcg atg gtg acg<br>Ala Ile Leu Cys Ser Ile Ser Tyr Leu Leu Gly Leu Ser Met Val Thr<br>                435                         440                    445 | 1344 |
| gag ggt ggc atg tat gtg ttt caa ctc ttt gac tac tat gca gct agt<br>Glu Gly Gly Met Tyr Val Phe Gln Leu Phe Asp Tyr Tyr Ala Ala Ser<br>450                        455                    460 | 1392 |
| ggt gta tgc ctt ttg tgg gtt gca ttc ttt gaa tgt ttt gtt att gcc<br>Gly Val Cys Leu Leu Trp Val Ala Phe Phe Glu Cys Phe Val Ile Ala<br>465                        470                    475                  480 | 1440 |
| tgg ata tat ggt ggt gat aac tta tat gac ggt att gag gac atg att<br>Trp Ile Tyr Gly Gly Asp Asn Leu Tyr Asp Gly Ile Glu Asp Met Ile<br>                  485                         490                    495 | 1488 |
| ggc tat cgg cct ggg ccc tgg atg aag tac agc tgg gct gtc atc act<br>Gly Tyr Arg Pro Gly Pro Trp Met Lys Tyr Ser Trp Ala Val Ile Thr<br>                    500                         505                    510 | 1536 |
| cca gtt ctc tgt gct gga tgt ttc atc ttc tct ctt gtc aag tat gta<br>Pro Val Leu Cys Ala Gly Cys Phe Ile Phe Ser Leu Val Lys Tyr Val<br>                515                         520                    525 | 1584 |
| ccc ctg acc tac aac aaa gtc tac gtg tat cct gat tgg gca att ggg<br>Pro Leu Thr Tyr Asn Lys Val Tyr Val Tyr Pro Asp Trp Ala Ile Gly<br>            530                         535                    540 | 1632 |
| ctg ggc tgg ggc ctg gcc cta tcc tcc atg gtg tgt atc ccc ttg gtc<br>Leu Gly Trp Gly Leu Ala Leu Ser Ser Met Val Cys Ile Pro Leu Val | 1680 |

```
                545                 550                 555                 560
att gcc atc ctc ctc tgc cgg acg gag gga ccg ttc cgc gtg aga atc     1728
Ile Ala Ile Leu Leu Cys Arg Thr Glu Gly Pro Phe Arg Val Arg Ile
                565                 570                 575 caa tac ctg ata acc ccc agg gag ccc aac cgc tgg gct gtg gag cgt     1776
Gln Tyr Leu Ile Thr Pro Arg Glu Pro Asn Arg Trp Ala Val Glu Arg
            580                 585                 590 gag ggg gcc aca ccc ttc cac tcc cgc aca agc ctc gtc atg aac ggc     1824
Glu Gly Ala Thr Pro Phe His Ser Arg Thr Ser Leu Val Met Asn Gly
            595                 600                 605 gca ctc atg aaa ccc agt cac gtc att gtg gag acc atg atg tga         1869
Ala Leu Met Lys Pro Ser His Val Ile Val Glu Thr Met Met
            610                 615                 620

<210> SEQ ID NO 2
<211> LENGTH: 622
<212> TYPE: PRT
<213> ORGANISM: Cricetulus griseus

<400> SEQUENCE: 2

Met Ala Thr Lys Glu Lys Leu Gln Cys Leu Lys Asp Phe His Lys Asp
1               5                   10                  15

Ile Leu Lys Pro Ser Pro Gly Lys Ser Pro Gly Thr Arg Pro Glu Asp
            20                  25                  30

Glu Ala Glu Gly Lys Pro Pro Gln Arg Glu Lys Trp Ser Ser Lys Ile
        35                  40                  45

Asp Phe Val Leu Ser Val Ala Gly Gly Phe Val Gly Leu Gly Asn Val
    50                  55                  60

Trp Arg Phe Pro Tyr Leu Cys Tyr Lys Asn Gly Gly Ala Phe Leu
65                  70                  75                  80

Ile Pro Tyr Phe Ile Phe Leu Phe Gly Ser Gly Leu Pro Val Phe Phe
                85                  90                  95

Leu Glu Val Ile Ile Gly Gln Tyr Thr Ser Glu Gly Gly Ile Thr Cys
            100                 105                 110

Trp Glu Lys Ile Cys Pro Leu Phe Ser Gly Ile Gly Tyr Ala Ser Ile
        115                 120                 125

Val Ile Val Ser Leu Leu Asn Val Tyr Tyr Ile Val Ile Leu Ala Trp
    130                 135                 140

Ala Thr Tyr Tyr Leu Phe His Ser Phe Gln Thr Glu Leu Pro Trp Ala
145                 150                 155                 160

His Cys Asn His Ser Trp Asn Thr Pro His Cys Met Glu Asp Thr Leu
                165                 170                 175

Arg Arg Asn Glu Ser Leu Trp Val Ser Leu Ser Ala Ser Asn Phe Thr
            180                 185                 190

Ser Pro Val Ile Glu Phe Trp Glu Arg Asn Val Leu Ser Leu Ser Ser
        195                 200                 205

Gly Ile Asp Glu Pro Gly Ala Leu Lys Trp Asp Leu Ala Leu Cys Leu
    210                 215                 220

Leu Leu Val Trp Leu Val Cys Phe Phe Cys Ile Trp Lys Gly Val Arg
225                 230                 235                 240

Ser Thr Gly Lys Val Val Tyr Phe Thr Ala Thr Phe Pro Phe Ala Met
                245                 250                 255

Leu Leu Val Leu Leu Val Arg Gly Leu Thr Leu Pro Gly Ala Gly Glu
            260                 265                 270

Gly Ile Lys Phe Tyr Leu Tyr Pro Asp Ile Ser Arg Leu Glu Asp Pro
        275                 280                 285
```

```
Gln Val Trp Ile Asp Ala Gly Thr Gln Ile Phe Phe Ser Tyr Ala Ile
    290                 295                 300
Cys Leu Gly Ala Met Thr Ser Leu Gly Ser Tyr Asn Lys Tyr Lys Tyr
305                 310                 315                 320
Asn Ser Tyr Arg Asp Cys Met Leu Leu Gly Cys Leu Asn Ser Gly Thr
                325                 330                 335
Ser Phe Val Ser Gly Phe Ala Val Phe Ser Ile Leu Gly Phe Met Ala
                340                 345                 350
Gln Glu Gln Gly Val Asp Ile Ala Asp Val Ala Glu Ser Gly Pro Gly
            355                 360                 365
Leu Ala Phe Ile Ala Tyr Pro Lys Ala Val Thr Met Met Pro Leu Pro
    370                 375                 380
Thr Phe Trp Ser Ile Leu Phe Phe Ile Met Leu Leu Leu Leu Gly Leu
385                 390                 395                 400
Asp Ser Gln Phe Val Glu Val Glu Gly Gln Ile Thr Ser Leu Val Asp
                405                 410                 415
Leu Tyr Pro Ser Phe Leu Arg Lys Gly Tyr Arg Arg Glu Val Phe Ile
                420                 425                 430
Ala Ile Leu Cys Ser Ile Ser Tyr Leu Leu Gly Leu Ser Met Val Thr
            435                 440                 445
Glu Gly Gly Met Tyr Val Phe Gln Leu Phe Asp Tyr Tyr Ala Ala Ser
    450                 455                 460
Gly Val Cys Leu Leu Trp Val Ala Phe Phe Glu Cys Phe Val Ile Ala
465                 470                 475                 480
Trp Ile Tyr Gly Gly Asp Asn Leu Tyr Asp Gly Ile Glu Asp Met Ile
                485                 490                 495
Gly Tyr Arg Pro Gly Pro Trp Met Lys Tyr Ser Trp Ala Val Ile Thr
            500                 505                 510
Pro Val Leu Cys Ala Gly Cys Phe Ile Phe Ser Leu Val Lys Tyr Val
    515                 520                 525
Pro Leu Thr Tyr Asn Lys Val Tyr Val Tyr Pro Asp Trp Ala Ile Gly
    530                 535                 540
Leu Gly Trp Gly Leu Ala Leu Ser Ser Met Val Cys Ile Pro Leu Val
545                 550                 555                 560
Ile Ala Ile Leu Leu Cys Arg Thr Glu Gly Pro Phe Arg Val Arg Ile
                565                 570                 575
Gln Tyr Leu Ile Thr Pro Arg Glu Pro Asn Arg Trp Ala Val Glu Arg
                580                 585                 590
Glu Gly Ala Thr Pro Phe His Ser Arg Thr Ser Leu Val Met Asn Gly
            595                 600                 605
Ala Leu Met Lys Pro Ser His Val Ile Val Glu Thr Met Met
    610                 615                 620
```